(12) United States Patent
Fujii et al.

(10) Patent No.: US 9,995,707 B2
(45) Date of Patent: Jun. 12, 2018

(54) GAS SENSOR

(71) Applicant: NGK SPARK PLUG CO., LTD., Nagoya-shi, Aichi (JP)

(72) Inventors: Tomoki Fujii, Kani (JP); Takaya Yoshikawa, Kasugai (JP)

(73) Assignee: NGK SPARK PLUG CO., LTD., Aichi (JP)

(*) Notice: Subject to any disclaimer, the term of this patent is extended or adjusted under 35 U.S.C. 154(b) by 79 days.

(21) Appl. No.: 15/170,845

(22) Filed: Jun. 1, 2016

(65) Prior Publication Data

US 2016/0274053 A1 Sep. 22, 2016

Related U.S. Application Data

(60) Division of application No. 14/074,861, filed on Nov. 8, 2013, now Pat. No. 9,733,207, which is a
(Continued)

(30) Foreign Application Priority Data

May 11, 2012 (JP) ................................. 2012-109860

(51) Int. Cl.
*G01N 27/00* (2006.01)
*G01N 7/00* (2006.01)
*G01N 27/407* (2006.01)

(52) U.S. Cl.
CPC ..... *G01N 27/4077* (2013.01); *G01N 27/4073* (2013.01); *G01N 27/4075* (2013.01)

(58) Field of Classification Search
CPC .......... G01N 27/00; G01N 7/00; G01N 21/00; G01N 31/00; G01N 33/00
(Continued)

(56) References Cited

U.S. PATENT DOCUMENTS

| 4,466,880 A | 8/1984 | Torii et al. |
| 2005/0022361 A1 | 2/2005 | Matsuo et al. |

(Continued)

FOREIGN PATENT DOCUMENTS

| JP | 58-48846 A | 3/1983 |
| JP | 58-91154 U | 6/1983 |

(Continued)

OTHER PUBLICATIONS

International Search Report (PCT/ISA/210) dated Jun. 11, 2013, issued in International Application No. PCT/JP2013/062664.
(Continued)

*Primary Examiner* — Brian J. Sines
(74) *Attorney, Agent, or Firm* — Sughrue Mion, PLLC

(57) ABSTRACT

A protector includes an inside protector having an inside peripheral wall and a front end wall in a front end side thereof and a tubular outside protector which surrounds the inside protector. In an outside peripheral wall of the outside protector, a plurality of outside introducing ports through which an external part of the outside protector communicates with a gas separating chamber are formed at equal intervals along a circumferential direction. The outside introducing ports are formed at positions nearer to the front end side than positions where inside introducing ports of the inside protector are formed. The outside introducing ports extend in the circumferential direction of the outside peripheral wall and formed in shapes of lateral holes in which opening lengths in the circumferential direction are larger than opening lengths in the direction perpendicular to the circumferential direction.

15 Claims, 26 Drawing Sheets

Related U.S. Application Data continuation-in-part of application No. PCT/JP2013/062664, filed on Apr. 30, 2013.

(58) Field of Classification Search
USPC .............. 422/83, 98; 73/31.05, 23.31, 21.32; 204/426, 428
See application file for complete search history.

(56) References Cited

U.S. PATENT DOCUMENTS

| | | | |
|---|---|---|---|
| 2005/0241937 A1 | 11/2005 | Shichida et al. | |
| 2007/0227228 A1* | 10/2007 | Yamauchi | G01N 27/4077 73/23.2 |
| 2007/0251823 A1* | 11/2007 | Yamada | G01N 27/4077 204/424 |
| 2008/0028831 A1* | 2/2008 | Nakashima | G01N 27/4077 73/31.05 |
| 2008/0067066 A1* | 3/2008 | Okumura | G01N 27/4077 204/424 |
| 2008/0105037 A1* | 5/2008 | Nakashima | G01N 27/4077 73/31.05 |
| 2010/0024524 A1* | 2/2010 | Ebner | G01N 27/4077 73/31.05 |
| 2010/0064663 A1* | 3/2010 | Goya | F01N 11/00 60/276 |
| 2013/0305809 A1* | 11/2013 | Fujita | G01D 11/245 73/31.05 |
| 2014/0138245 A1 | 5/2014 | Fujii et al. | |

FOREIGN PATENT DOCUMENTS

| | | |
|---|---|---|
| JP | 60-233542 A | 11/1985 |
| JP | 63-87559 U | 6/1988 |
| JP | 64-23661 U | 2/1989 |
| JP | 2-148464 U | 12/1990 |
| JP | 10-253576 A | 9/1998 |
| JP | 10-253577 A | 9/1998 |
| JP | 2003-43002 A | 2/2003 |
| JP | 2004-109125 A | 4/2004 |
| JP | 2005-37372 A | 2/2005 |
| JP | 2011-21994 A | 2/2011 |
| JP | 2011-145145 A | 7/2011 |
| JP | 2012-185113 A | 9/2012 |
| WO | 2013/168649 A1 | 11/2013 |

OTHER PUBLICATIONS

Written Opinion (PCT/ISA/236) dated Jun. 11, 2013, issued in International Application No. PCT/JP2013/062664.

Communication dated Aug. 10, 2016, issued by the Japanese Intellectual Property Office in counterpart Japanese Patent Application No. 2013-229027.

* cited by examiner

GAS SENSOR

CROSS-REFERENCE TO RELATED APPLICATIONS

This is a Divisional Application of U.S. application Ser. No. 14/074,861 filed Nov. 8, 2013 which is a Continuation-In-Part Application (CIP) of International Application No. PCT/JP2013/062664 filed Apr. 30, 2013, which claims benefit of Japanese Patent Application No. 2012-109860 filed May 11, 2012. The above-noted applications are incorporated herein by reference in their entirety.

BACKGROUND

The present invention relates to a gas sensor provided with a protector which protects a sensing element exposed to gas to be detected from being covered with water.

Usually, a gas sensor is known which includes a sensing element in which electric motive forces different in level are generated or an element resistance changes depending on the concentration of specific gas, for instance, NOx (nitrogen oxide) or oxygen in exhaust gas of a motor vehicle. This gas sensor is attached to an exhaust pipe of the motor vehicle and used. When the sensing element is heated or exposed to the exhaust gas of high temperature, a temperature of the sensing element is high. On the other hand, when moisture (water droplet) included in the exhaust gas adheres to the sensing element (the sensing element is covered with water) so that the sensing element receives a thermal shock, there is a fear that cracks or breaks may be probably formed. Thus, to the gas sensor, a protector which covers the sensing element is attached, so that the sensing element is protected from being covered with water.

For instance, in a gas sensor disclosed in patent literature 1, a protector has a double structure including an inside protector with which a sensing element is covered and an outside protector with which the inside protector is covered. In the outside protector, a gas introducing port is formed for introducing exhaust gas to an inner part. An opening area of the gas introducing port needs to be restricted to reduce an entry of condensed water to the protector, however, the opening area for introducing the exhaust gas is necessary to a certain degree. Accordingly, in the gas sensor disclosed in JP-A-2011-145145, the gas introducing port is formed in the shape of a hole elongated in the axial direction of the gas sensor.

SUMMARY

However, as shown in FIG. 15, when a gas introducing port is a hole elongated in a longitudinal direction, when a water droplet passes through the hole and enters from an upper part of the gas introducing port, since a gas introducing port of an inside protector is located just near to the gas introducing port, a problem arises that there is a high risk that an element may be probably covered with water.

The present invention is devised by solving the above-described problem and it is an object of the present invention to provide a gas sensor which can assuredly prevent a sensing element from being covered with water without lowering an introducing efficiency of exhaust gas to a protector which covers the sensing element.

According to a first exemplary embodiment of the present invention, a gas sensor is provided that includes a sensing element which extends in an axial direction and has in a front end side a detecting part for detecting a specific gas component in gas to be detected, a metal shell which surrounds and holds a periphery of the sensing element in a radial direction under a state that the detecting part is allowed to protrude from a front end part of itself, an inside protector which has an inside peripheral wall and a front end wall in a front end side thereof, an opening end part of a base end side fixed to the front end part of the metal shell under a state that the detecting part is accommodated so as to directly face an inner part of itself and inside introducing ports formed at positions opposed to the sensing element on the inside peripheral wall to introduce the gas to the inner part of itself, and an outside protector which has an outside peripheral wall so as to surround the inside peripheral wall with a cavity provided between the inside peripheral wall and the outside peripheral wall and has outside introducing ports formed on the outside peripheral wall to introduce the gas into the cavity, and is characterized in that either the plurality of inside introducing ports or the plurality of outside introducing ports are provided in a circumferential direction of at least one of the inside peripheral wall and the outside peripheral wall and are formed in shapes of lateral holes in which opening lengths in the circumferential direction are larger than opening lengths in the direction perpendicular to the circumferential direction.

In the gas sensor of the first exemplary embodiment, either the plurality of inside introducing ports or the plurality of outside introducing ports are provided in the circumferential direction of at least one of the inside peripheral wall and the outside peripheral wall and are formed in the shapes of the lateral holes in which the opening lengths in the circumferential direction are larger than the opening lengths in the direction perpendicular to the circumferential direction. Accordingly, the sensing element can be more assuredly prevented from being covered with water without lowering an introducing efficiency of exhaust gas to the protector which covers the sensing element than in a gas sensor which has introducing ports formed in shapes of holes elongated in the axial direction of the gas sensor. Thus, water droplets can be prevented from adhering to the sensing element to break the sensing element.

According to a second exemplary embodiment of the present invention, a gas sensor is provided that includes a sensing element which extends in an axial direction and has in a front end side a detecting part for detecting a specific gas component in gas to be detected, a metal shell which surrounds and holds a periphery of the sensing element in a radial direction under a state that the detecting part is allowed to protrude from a front end part of itself, an inside protector which has an inside peripheral wall and a front end wall in a front end side thereof, an opening end part of a base end side fixed to the front end part of the metal shell under a state that the detecting part is accommodated so as to directly face an inner part of itself and inside introducing ports formed at positions opposed to the sensing element on the inside peripheral wall to introduce the gas to be detected to the inner part of itself, and an outside protector which has an outside peripheral wall so as to surround the inside peripheral wall with a cavity provided between the inside peripheral wall and the outside peripheral wall and has outside introducing ports formed on the outside peripheral wall to introduce the gas to be detected into the cavity, and is characterized in that either the plurality of inside introducing ports or the plurality of outside introducing ports are a plurality of hole parts provided in a circumferential direction of at least one of the inside peripheral wall and the outside peripheral wall and the one hole part is a hole part corresponding to a lateral hole which is formed in such a way that a plurality of hole parts of shapes of longitudinal holes in which opening lengths in the circumferential direction are smaller than opening lengths in the direction perpendicular to the circumferential direction are allowed to come close together in the circumferential direction.

In the gas sensor of the second exemplary embodiment, the introducing ports formed in the protector are the plurality of hole parts provided in the circumferential direction of the peripheral wall and the one hole part is a hole part corresponding to a lateral hole which is formed in such a way that a plurality of the hole parts of the shapes of the longitudinal holes in which the opening lengths in the circumferential direction are smaller than the opening lengths in the direction perpendicular to the circumferential direction are allowed to come close together in the circumferential direction. Accordingly, strength of a part of the introducing port is not deteriorated and an introducing efficiency of exhaust gas to the protector which covers the sensing element is not deteriorated. Further, the sensing element can be more assuredly prevented from being covered with water than that of a gas sensor which has introducing ports formed in shapes of holes elongated in the axial direction of the gas sensor. Accordingly, water droplets can be prevented from adhering to the sensing element to break the sensing element.

Further, when a length of the outer periphery of the outside peripheral wall of the outside protector is set to L1, and if a total of lengths of the outside introducing ports in the circumferential direction is set to L2 when the outside peripheral wall of the outside protector is projected on a plane vertical to the axial direction, L2/L1 may be set to 0.3 or more. When the L2/L1 is 0.3 or more, a ventilation of the outside introducing ports is sufficient and a responsiveness of the sensing element 10 is not deteriorated. Further, the sensing element can be more assuredly prevented from being covered with water than that of a gas sensor which has outside introducing ports formed in shapes of holes elongated in the axial direction of the gas sensor.

When a length of an outer periphery of the inside peripheral wall of the inside protector is set to L5, and if a total of lengths of the inside introducing ports in the circumferential direction is set to L6 when the inside peripheral wall of the inside protector is projected on a plane vertical to the axial direction, L6/L5 may be set to 0.3 or more. When the L6/L5 is 0.3 or more, a ventilation of the inside introducing ports is sufficient and a responsiveness of the sensing element 10 is not deteriorated. Further, the sensing element can be more assuredly prevented from being covered with water than that of a gas sensor which has inside introducing ports formed in shapes of holes elongated in the axial direction of the gas sensor.

Further, L2/L1 or L6/L5 may be set to 0.52 or more. In this case, the ventilation of the outside introducing ports or the inside introducing ports is sufficient as the lateral holes and the responsiveness of the sensing element 10 is not deteriorated. Further, the sensing element can be more assuredly prevented from being covered with water than that of a gas sensor which has outside introducing ports or inside introducing ports formed in shapes of holes elongated in the axial direction of the gas sensor.

Further, when a length of the outside introducing port in the circumferential direction of the outside peripheral wall of the outside protector is set to L3 and a length of the outside introducing port in the direction perpendicular to L3 is set to L4, L3/L4 may be set to 3 or more. In this case, the outside introducing port can sufficiently function as the lateral hole.

Further, when a length of the inside introducing port in the circumferential direction of the inside peripheral wall of the inside protector is set to L7 and a length of the inside introducing port in the direction perpendicular to L7 is set to L8, L7/L8 may be set to 3 or more. In this case, the inside introducing port can sufficiently function as the lateral hole.

Further, when a circular section formed by cutting the outside protector by a plane which is perpendicular to the axial direction and passes the outside introducing ports is divided into a plurality of parts by a straight line passing through a center thereof, at least one outside introducing port may be present in each of the divided areas. In this case, since the outside introducing ports are provided respectively in the divided areas, a rotating angle for attachment of the gas sensor to an exhaust gas passage is not limited.

Further, when a circular section formed by cutting the inside protector by a plane which is perpendicular to the axial direction and passes the inside introducing ports is divided into a plurality of parts by a straight line passing through a center thereof, at least one inside introducing port may be present in each of the divided areas. In this case, since the inside introducing ports are provided respectively in the divided areas, a rotating angle for attachment of the gas sensor to an exhaust gas passage is not limited.

Further, the outside introducing port may be formed by at least one of the hole parts in the shapes of the lateral holes and the hole parts corresponding to the lateral holes.

Further, the inside introducing port may be formed by at least one of the hole parts in the shapes of the lateral holes and the hole parts corresponding to the lateral holes.

Further, the outside introducing ports may be provided at other positions than positions opposed to the inside introducing ports on the outside peripheral wall of the outside protector.

In this case, since the outside introducing ports are provided at other positions than the positions opposed to the inside introducing ports on the outside peripheral wall of the outside protector, water droplets which enter from the outside introducing ports do not reach the inside introducing ports and collide with the inside peripheral wall of the inside protector. Accordingly, the sensing element can be assuredly prevented from being covered with water. Further, an introducing efficiency of exhaust gas to the protector which covers the sensing element is not deteriorated.

Further, the outside introducing ports may be provided nearer to the front end side in the axial direction on the outside peripheral wall of the outside protector than the inside introducing ports located nearest to the base end side. The water droplets which enter from the outside introducing ports do not reach the inside introducing ports and collide with the inside peripheral wall of the inside protector and are discharged from the front end side of the outside protector. Accordingly, the sensing element can be assuredly prevented from being covered with water.

Further, the plurality of outside introducing ports may be provided in the axial direction in the outside peripheral wall of the outside protector. In this case, a quantity of exhaust gas which enters from the outside introducing ports is sufficient and a response of a detection value of the sensing element to the exhaust gas is not delayed. Further, since the outside introducing ports are provided over an entire periphery of the outside peripheral wall of the outside protector, a rotating angle for attachment of the gas sensor to an exhaust gas passage is not limited.

Further, the plurality of inside introducing ports may be provided in the axial direction in the inside peripheral wall of the inside protector. In this case, a quantity of exhaust gas which enters from the outside introducing ports is sufficient and a response of a detection value of the sensing element to the exhaust gas is not delayed. Further, since the inside introducing ports are provided over an entire periphery of the inside peripheral wall of the inside protector, a rotating angle for attachment of the gas sensor to an exhaust gas passage is not limited.

DESCRIPTION OF EXEMPLARY EMBODIMENTS

Figure 1:
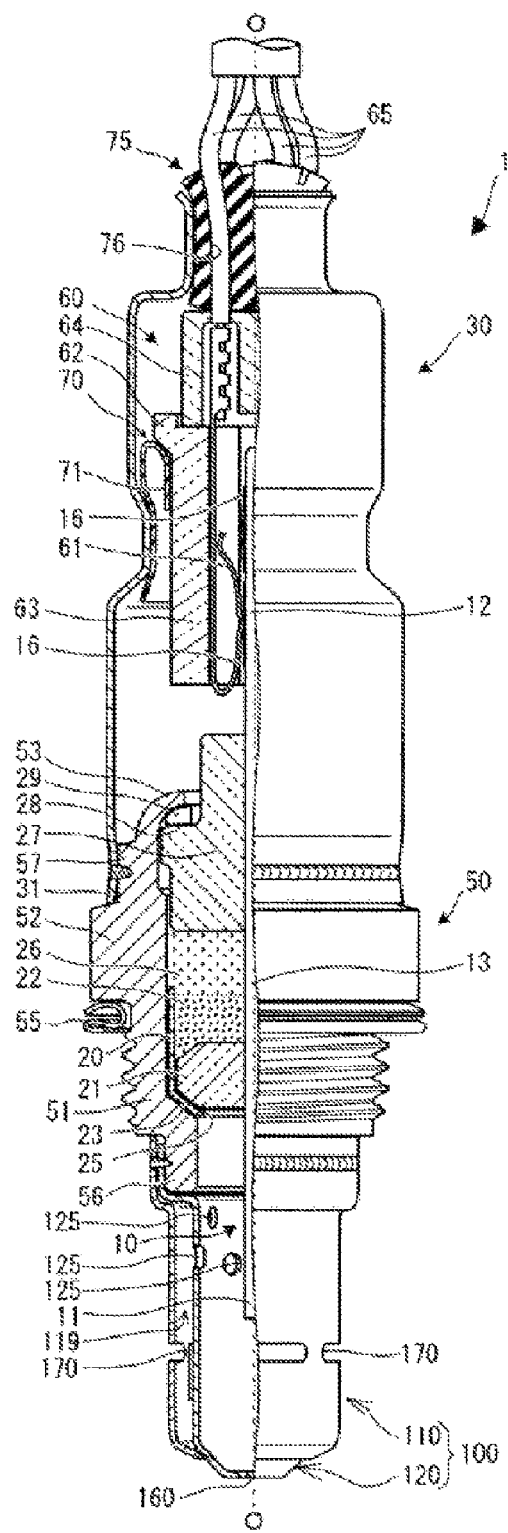
FIG. 1 is a partly sectional view of a gas sensor 1.
Figure 2:
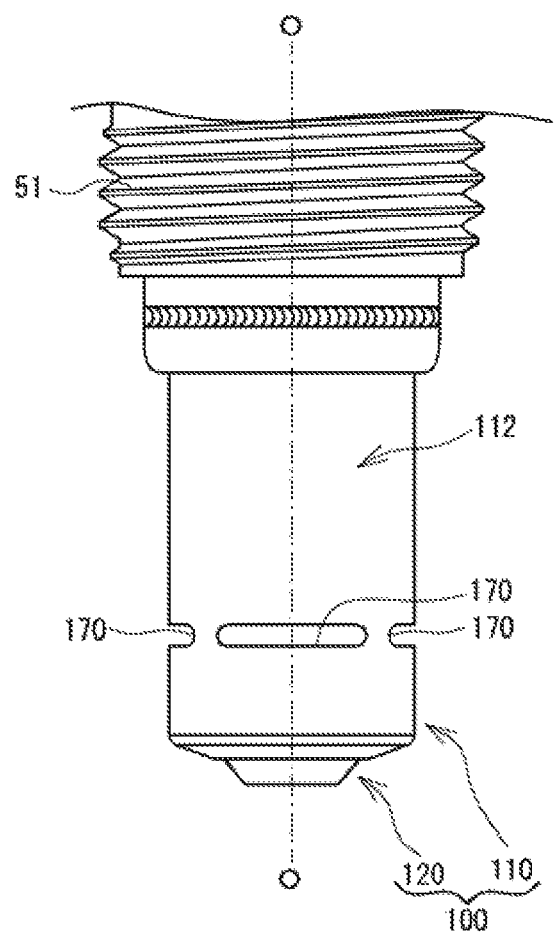
FIG. 2 is a front view of a protector 100 according to a first exemplary embodiment viewed from the same direction as that of FIG. 1.
Figure 3:
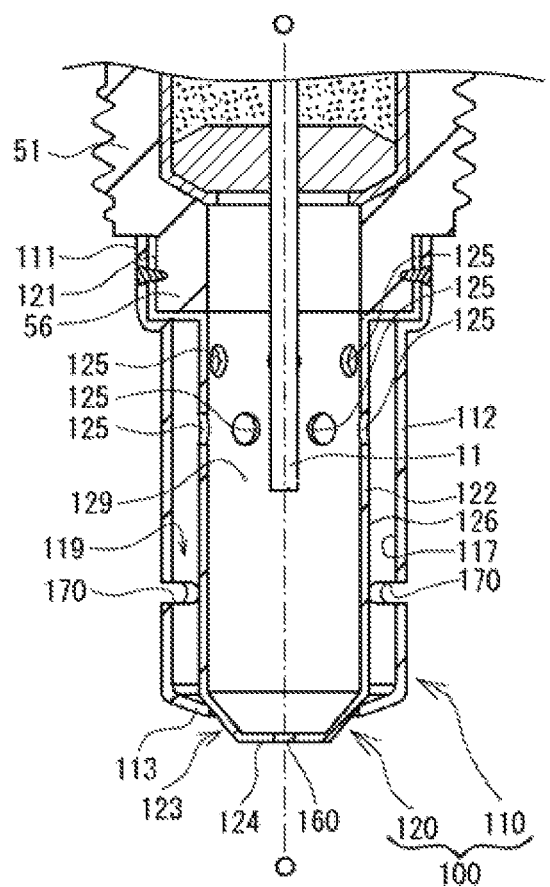
FIG. 3 is a longitudinally sectional view of the protector 100 according to the first exemplary embodiment in the same direction as that of a section shown in FIG. 1.

Now, a first exemplary embodiment of a gas sensor which embodies the present invention will be described below with reference to FIG. 1 to FIG. 3. In FIG. 1 to FIG. 3, a direction of an axis O (shown by a dashed line) of the gas sensor 1 is shown as a vertical direction. A side of detecting part 11 of a sensing element 10 held in an inner part is described as a front end side of the gas sensor 1 and a side of a rear end part 12 (see FIG. 2) is described as a rear end side of the gas sensor 1.

The gas sensor 1 shown in FIG. 1 illustrates, as one example, what is called an oxygen sensor that is attached to an exhaust pipe (not shown in the drawing) of a motor vehicle and includes a detecting part 11 of a sensing element 10 held in an inner part which is exposed to exhaust gas circulating in the exhaust pipe to detect a concentration of oxygen as gas to be detected included in the exhaust gas.

The sensing element 10 includes a gas detector formed in the shape of a thin plate extending in the axial direction O, as well-known, to detect a concentration of oxygen and a heater body which heats to early activate the gas detector, which are stuck to each other and integrally formed in the configuration of a substantially prismatic laminated body.

In FIG. 1 and FIG. 2, a transverse direction of a sheet surface is shown as a direction of thickness of the plate and a front and back side direction of the sheet surface is shown as a direction of width of the plate. The gas detector is formed with a solid electrolyte including zirconia as a main component or a detecting electrode including platinum as a main component (not shown in the drawing). The detecting electrode is arranged in the detecting part 11 in the front end side of the sensing element 10. In the rear end part 12 in the rear end side of the sensing element 10, six electrode pads 16 (two of them are shown in FIG. 1) are formed to take out an electrode from the gas detector or the heater body. In the present exemplary embodiment, the sensing element 10 is described as a "sensing element" in the present invention. However, strictly, the heater body is not necessarily required as a structure of the sensing element and the gas detector corresponds to the "sensing element" of the present invention.

A metal cup 20 made of metal which has a bottomed tubular form and has an opening 25 in a bottom wall is arranged at a position somewhat nearer to the front end side than to a central part of a drum part 13 of the sensing element 10. The sensing element 10 is inserted into the metal cup 20 through the opening 25. The detecting part 11 is allowed to protrude from the opening 25 to the front end side. The metal cup 20 is a member which holds the sensing element 10 in a metal shell 50. A front end peripheral edge part 23 which is tapered from the bottom wall to an outer peripheral wall is formed in an edge part of the bottom wall. A ceramic ring 21 made of alumina and a talc ring 22 formed by compressing and hardening talc powder surround the periphery of the sensing element 10 are arranged in layers in the axial direction O and accommodated in the metal cup 20. The talc ring 22 is smashed in the metal cup 20 to fill minute parts therewith. Thus, the sensing element 10 is positioned and held in the metal cup 20.

The sensing element 10 formed integrally with the metal cup 20 is surrounded and held in its periphery by the tubular metal shell 50 made of low carbon steel such as SUS 430. The metal shell 50 is a member which serves to attach the gas sensor 1 to the exhaust pipe (not shown in the drawing) of the motor vehicle. An attaching part 51 which has an external thread formed for an attachment to the exhaust pipe is provided in a front end side of an outer periphery thereof. A front end engaging part 56 with which a below-described protector 100 is engaged is formed in the front end side from the attaching part 51. A tool engaging part 52 with which an attaching tool is engaged is formed in a center of the outer periphery of the metal shell 50. A rear end engaging part 57 with which a below-described outer tube 30 is engaged is formed in a rear end side of the tool engaging part 52. Further, a cramping part 53 which cramps and holds the sensing element 10 in the metal shell 50 is formed in a rear end side thereof. An annular gasket 55 between the tool engaging part 52 and the attaching part 51 is inserted to prevent gas from being degassed or purged when the gas sensor is attached to the exhaust pipe.

In an inner periphery of the metal shell 50, a stepped part is provided in the vicinity of the attaching part 51. The front end peripheral edge part 23 of the above-described metal cup 20 which holds the sensing element 10 is engaged with the stepped part. Then, the inner periphery of the metal shell 50 is filled with a talc ring 26 from the rear end side of the metal cup 20 with the sensing element 10 inserted to the talc ring 26 itself. Further, a tubular sleeve 27 is fitted into the metal shell 50 with the sensing element 10 inserted to the tubular sleeve 27 itself so as to press the talc ring 26 from the rear end side. A stepped shoulder part 28 is formed in an outer periphery of the rear end side of the sleeve 27. A circular annular packing 29 is arranged in the shoulder part 28. Under this state, the cramping part 53 of the metal shell 50 is crimped inward to press the shoulder part 28 of the sleeve 27 to the front end side through the packing 29. By this crimping operation, the talc ring 26 pressed by the sleeve 27 is smashed in the metal shell 50 to fill the inner periphery therewith to minute parts. Thus, the metal cup 20 and the sensing element 10 are positioned and held in the metal shell 50 by the talc ring 26 and the talc ring 22 previously charged in the metal cup 20.

The rear end part 12 of the sensing element 10 is allowed to protrude more rearward than a rear end (the cramping part 53) of the metal shell 50. The rear end part 12 is covered with a tubular separator 60 made of insulation ceramics. The separator 60 includes a front end side separator 63 and a rear end side separator 64. The rear end side separator 64 is engaged with a collar shaped collar part 62 provided in the front end side separator 63. The front end side separator 63 accommodates and holds therein connecting parts of the six electrode pads 16 formed in the rear end part 12 of the sensing element 10 and six connecting terminals 61 (one of them is shown in FIG. 1) electrically connected to the electrode pads 16 respectively. The rear end side separator 64 accommodates therein connecting parts of the connecting terminals 61 and six lead wires 65 (four of them are shown in FIG. 1) pulled out from the gas sensor 1.

The tubular outer tube 30 formed with stainless steel (for instance, SUS304) is arranged so as to surround a periphery of the rear end part 12 of the sensing element 10 to which the separator 60 is fitted. The outer tube 30 has an opening end 31 of the front end side engaged with an outer periphery of the rear end engaging part 57 of the metal shell 50. The opening end 31 is cramped from an outer peripheral side and further joined to the rear end engaging part 57 by applying a laser beam welding process around the outer periphery. Thus, the outer tube 30 is formed integrally with the metal shell 50.

Further, a tubular holding metal shell 70 made of metal is arranged in a gap between the outer tube 30 and the front end side separator 63. The holding metal shell 70 has a support part 71 formed by bending inside a rear end of itself. The collar part 62 of the front end side separator 63 which is inserted to the support part 71 itself is engaged with the support part 71 to hold the front end side separator 63. Under this state, an outer peripheral surface of the outer tube 30 in the part where the holding metal shell 70 is arranged is cramped inward, so that the holding metal shell 70 which supports the front end side separator 63 is fixed to the outer tube 30.

Then, a grommet 75 made of fluoro rubber is fitted to an opening in the rear end side of the outer tube 30. The grommet 75 has six insert holes 76 (one of them is shown in FIG. 1). The above-described six lead wires 65 pulled out from the separator 60 are air-tightly inserted into the insert holes 76 respectively. Under this state, the grommet 75 presses the rear end side separator 64 to the front end side separator 63 and is cramped from the outer periphery of the outer tube 30 so that the grommet is fixed to the rear end of the outer tube 30.

On the other hand, the detecting part 11 of the sensing element 10 held in the metal shell 50 is allowed to protrude from the front end part (the front end engaging part 56) of the metal shell 50. The protector 100 is fitted to the front end engaging part 56 by a spot welding or a laser beam welding. The protector 100 is a member which serves to protect the detecting part 11 of the sensing element 10 from dirt by a deposit (poisoning adhering materials such as fuel ash content or oil component) in the exhaust gas or a break due to a cover with water Now, a structure of the protector 100 according to a first exemplary embodiment will be described below with reference to FIG. 2 and FIG. 3. The protector 100 shown in FIG. 2 and FIG. 3 has a double structure which includes a bottomed cylindrical inside protector 120 having an inside peripheral wall 122 and a front end wall 124 in a front end side thereof and a tubular outside protector 110 which surrounds a radial periphery of the inside peripheral wall 122 by an outside peripheral wall 112. A gas separating chamber 119 which is formed with a cavity is provided Between an outer surface 126 of the inside peripheral wall 122 of the inside protector 120 and an inner surface 117 of the outside peripheral wall 112 of the outside protector 110.

The inside protector 120 has an outside diameter formed to be smaller than that of the front end engaging part 56 of the metal shell 50 and accommodates the detecting part 11 of the sensing element 10 in such a manner as to directly face the detecting part 11. Further, a base end part 121 of an opening end side (the rear end side) is enlarged in its diameter so as to be engaged with an outer periphery of the front end engaging part 56. Further, a peripheral edge part of the front end wall 124 is formed as a tapered part 123 expanded toward the inside peripheral wall 122 in a tapered form. In the inside peripheral wall 122 of the inside protector 120, a plurality (12 pieces in the present exemplary embodiment) of inside introducing ports 125 are opened in the circumferential direction at positions near to the base end part 121 in the axial direction O and opposed to the detecting part 11 of the sensing element 10. The inside introducing ports 125 are holes which mainly introduce a gas component of the exhaust gas introduced to the gas separating chamber 119 through below-described outside introducing ports 170 of the outside protector 110 to an inner part of the inside protector 120, namely, a gas detecting chamber 129 to which the detecting part 11 of the sensing element 10 is exposed.

Further, the laser beam welding is applied from an outer periphery of the base end part 121 including the below-described outside protector 110. Thus, the inside protector 120 is fixed to the front end engaging part 56 of the metal shell 50. Then, an exhaust port 160 is opened to the front end wall 124 of the inside protector 120. Water droplets which enter the inside protector 120 (the gas detecting chamber 129) are exhausted outside the protector 100 through the exhaust port 160. Further, the gas component introduced to the gas detecting chamber 129 through the inside introducing ports 125 is also exhausted outside through the exhaust port 160, so that a gas exchange is carried out in the gas detecting chamber 129.

Then, in the outside protector 110, one opened end is enlarged in its diameter and engaged with the outer periphery of the base end part 121 of the inside protector 120 as a base end part 111. Under a state that the base end part 111 of the outside protector 110 is overlapped on the base end part 121 of the inside protector 120, the laser beam welding that passes through the base end part 121 and reaches to the front end engaging part 56 of the metal shell 50 (see FIG. 1) is applied around an outer periphery of the base end part 111 from an outer peripheral surface side of the base end part 111. Thus, the outside protector 110 and the inside protector 120 are fixed to the metal shell 50.

Further, a front end part 113 of the outside protector 110 is bent inside in the vicinity of the tapered part 123 of the inside protector 120. Thus, the cavity between the outer surface 126 of the inside peripheral wall 122 of the inside protector 120 and the inner surface 117 of the outside protector 110 is closed in the front end side to form the above-described gas separating chamber 119. Then, the tapered part 123 with the tapered form of the inside protector 120 is allowed to protrude more to the front end side in the axial direction O than the front end part 113 of the outside protector 110. The front end part 113 of the outside protector 110 and the tapered part 123 of the inside protector 120 which respectively have different angles form a continuous taper.

Subsequently, the plurality (four pieces in the present exemplary embodiment) of outside introducing ports 170 through which an external part of the outside protector 110 communicates with the gas separating chamber 119 are formed in the outside peripheral wall 112 of the outside protector 110 at equal intervals along the circumferential direction. The outside introducing ports 170 are formed at positions nearer to the front end side than the positions where the inside introducing ports 125 of the inside protector 120 are formed in the axial direction O (namely, positions of rear ends of the outside introducing ports 170 are arranged at positions nearer to the front end side than positions of front ends of the inside introducing ports 125). Accordingly, the outside introducing ports 170 are provided at other positions than positions opposed to the inside introducing ports 125 in the outside peripheral wall 112 of the outside protector 110. Further, the outside introducing ports 170 extend in the circumferential direction of the outside peripheral wall 112 and formed in shapes of lateral holes in which opening lengths in the circumferential direction are larger than opening lengths in the direction perpendicular to the circumferential direction. A relation between the length of the outside introducing port 170 in the circumferential direction and the length of an outer periphery of the outside peripheral wall 112 will be described below.

When the gas sensor 1 having the above-described structure is attached to the exhaust pipe of an internal combustion engine, the gas sensor is attached thereto with the front end side in the axial direction O directed downward in the direction of gravity and the front end side more to the exhaust pipe than the attaching part 51 of the metal shell 50 is exposed. The exhaust gas circulating in the exhaust pipe collides with the protector 100 shown in FIG. 2 from a direction (for instance, a direction perpendicular to the axial direction O) at least different from the axial direction O and is introduced to the gas separating chamber 119 from the outside introducing ports 170 of the outside protector 110. At this time, relatively heavy moisture (the water droplet) and a relatively light gas component included in the exhaust gas are separated. At that time, since the outside introducing ports 170 are formed at the positions nearer to the front end side than the positions where the inside introducing ports 125 of the inside protector 120 are formed in the axial direction O and formed along the circumferential direction of the outside peripheral wall 112 of the outside protector 110, the water droplets which enter the gas separating chamber 119 from the outside introducing ports 170 can be prevented from entering the gas detecting chamber 129 from the inside introducing ports 125 of the inside protector 120. Further, since the plurality of outside introducing ports 170 are formed so as to have prescribed lengths along the circumferential direction of the outside peripheral wall 112 of the outside protector 110, a quantity of the exhaust gas which enters the gas separating chamber 119 from the outside introducing ports 170 is sufficient and a response of a detection value of the sensing element 10 to the exhaust gas is not delayed.

Figure 4:
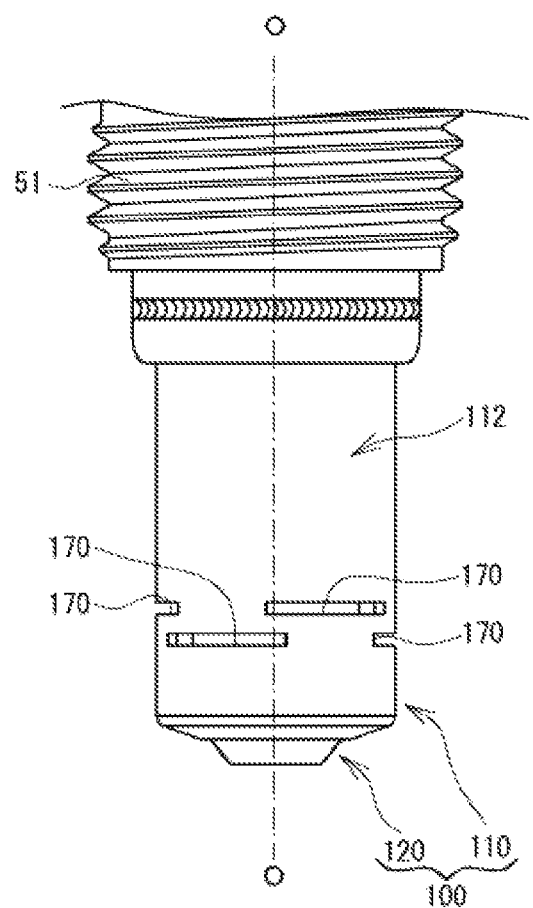
FIG. 4 is a front view of a protector 100 according to a second exemplary embodiment.
Figure 5:
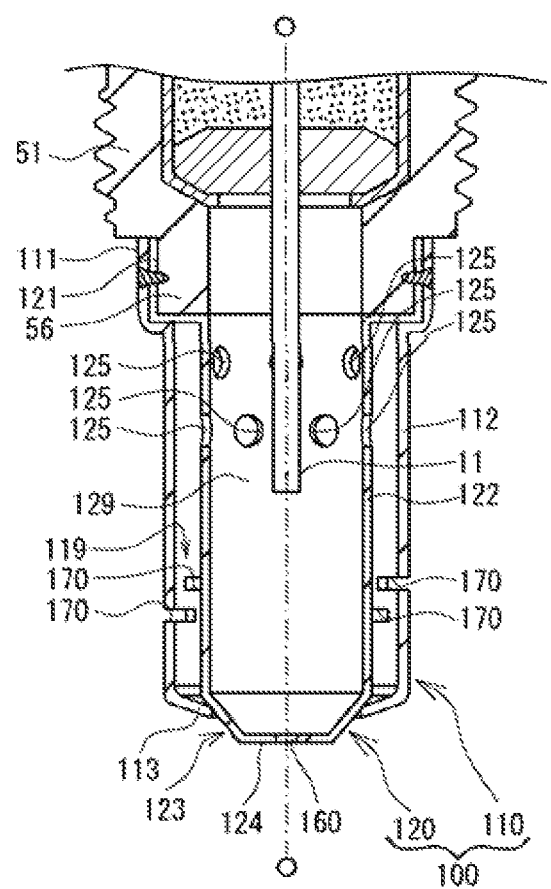
FIG. 5 is a longitudinally sectional view of the protector 100 according to the second exemplary embodiment in the same direction as that of the section shown in FIG. 1.

Now, referring to FIG. 4 and FIG. 5, a protector 100 of a gas sensor 1 according to a second exemplary embodiment will be described below. In the gas sensor 1 according to the second exemplary embodiment, a structure of an outside introducing port 170 of an outside protector 110 is merely different from that of the first exemplary embodiment, and other structures are the same. Thus, only a different point will be described below.

Now, the structure of the outside introducing port 170 of the outside protector 110 according to the second exemplary embodiment will be described below. In an outside peripheral wall 112 of the outside protector 110 according to the second exemplary embodiment, a plurality of outside introducing ports 170 through which an external part of the outside protector 110 communicates with a gas separating chamber 119 are formed along a circumferential direction. The outside introducing ports 170 extend in the circumferential direction of the outside peripheral wall 112 and are formed in shapes of lateral holes in which opening lengths in the circumferential direction are larger than opening lengths in the direction perpendicular to the circumferential direction. Further, the outside introducing ports 170 are formed in two rows in an axial direction O on the outside peripheral wall 112. Further, the outside introducing ports 170 are arranged at equal intervals in the circumferential direction of the outside peripheral wall 112 so that an end part of the one outside introducing port 170 is overlapped on the other outside introducing port 170 in the axial direction O. Further, all the outside introducing ports 170 are formed at positions nearer to a front end side than positions where inside introducing ports 125 of an inside protector 120 are formed in the axial direction O. Namely, the positions of rear ends of the outside introducing ports 170 are arranged nearer to the front end side than the positions of front ends of the inside introducing ports 125.

In addition to the effects of the second exemplary embodiment, in the outside protector 110 according to the second exemplary embodiment, since the outside introducing ports 170 are formed in the two rows on the outside peripheral wall 112 of the outside protector 110 and arranged at equal intervals in the circumferential direction of the outside peripheral wall 112 so that the end part of the one outside introducing port 170 is overlapped on the other outside introducing port 170, a quantity of exhaust gas which enters the gas separating chamber 119 from the outside introducing ports 170 is sufficient and a response of a detection value of a sensing element 10 to the exhaust gas is not delayed. Further, since all the outside introducing ports 170 are formed at the positions nearer to the front end side than the positions where the inside introducing ports 125 of the inside protector 120 are formed in the axial direction O, water droplets which enter the gas separating chamber 119 from the outside introducing ports 170 can be prevented from entering a gas detecting chamber 129 from the inside introducing ports 125 of the inside protector 120. Further, since the outside introducing ports 170 are provided over an entire periphery of the outside peripheral wall 112 of the outside protector 110, a rotating angle for attachment of the gas sensor 1 to an exhaust gas passage is not limited.

Figure 6:
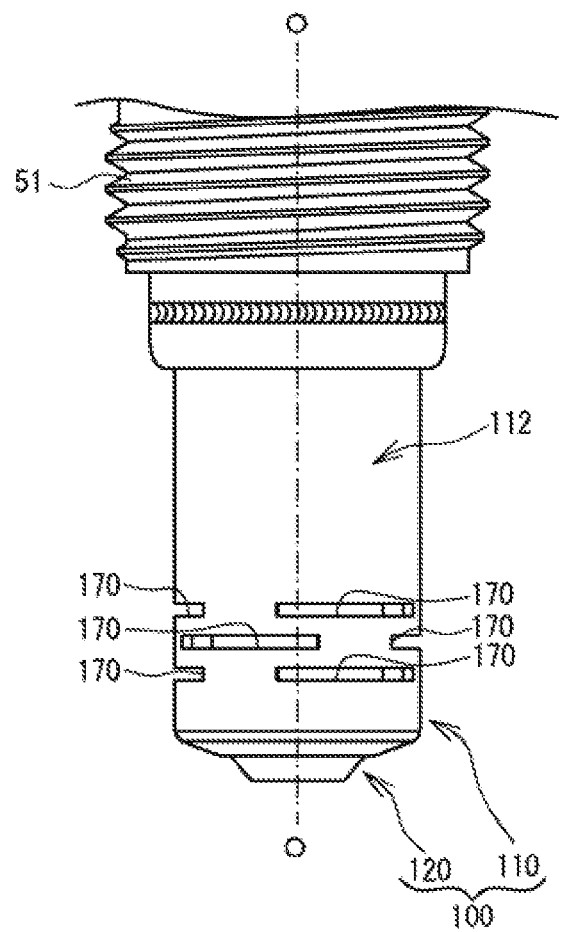
FIG. 6 is a front view of a protector 100 according to a third exemplary embodiment.
Figure 7:
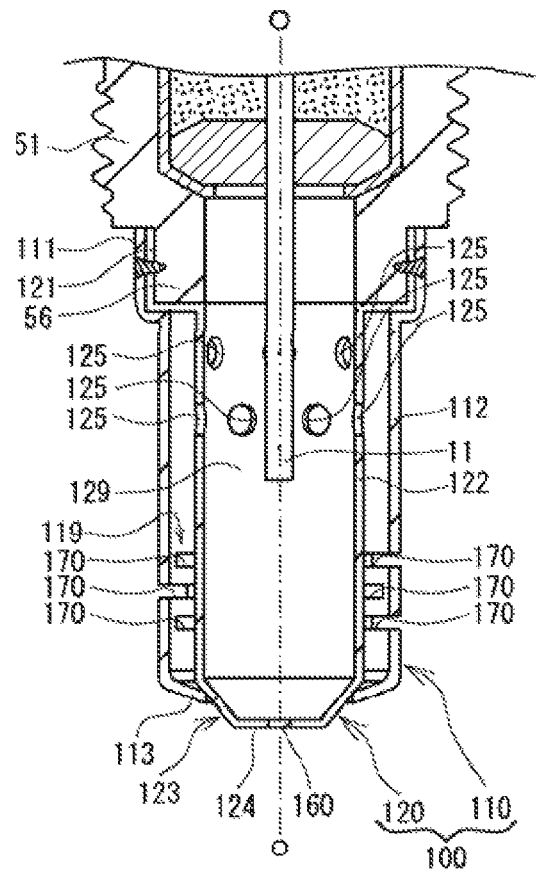
FIG. 7 is a longitudinally sectional view of the protector 100 according to the third exemplary embodiment in the same direction as that of the section shown in FIG. 1.

Now, referring to FIG. 6 and FIG. 7, a protector 100 of a gas sensor 1 according to a third exemplary embodiment will be described below. In the gas sensor 1 according to the third exemplary embodiment, a structure of an outside introducing port 170 of an outside protector 110 is merely different from that of the first exemplary embodiment, and other structures are the same. Thus, only a different point will be described below.

In an outside peripheral wall 112 of the outside protector 110 according to the third exemplary embodiment, a plurality of outside introducing ports 170 through which an external part of the outside protector 110 communicates with a gas separating chamber 119 are formed along a circumferential direction. The outside introducing ports 170 extend in the circumferential direction of the outside peripheral wall 112 and are formed in shapes of lateral holes in which opening lengths in the circumferential direction are larger than opening lengths in the direction perpendicular to the circumferential direction. Further, the outside introducing ports 170 are formed in three rows in an axial direction O on the outside peripheral wall 112. Further, the outside introducing ports 170 are arranged in the outside peripheral wall 112 so that an end part of the one outside introducing port 170 is overlapped on the other outside introducing port 170 in the axial direction O. Further, all the outside introducing ports 170 are formed at positions nearer to a front end side than positions where inside introducing ports 125 of an inside protector 120 are formed in the axial direction O. Namely, the positions of rear ends of the outside introducing ports 170 are arranged nearer to the front end side than the positions of front ends of the inside introducing ports 125.

In addition to the effects of the first and second exemplary embodiments, in the outside protector 110 according to the third exemplary embodiment, since the outside introducing ports 170 are formed in the three rows on the outside peripheral wall 112 of the outside protector 110 and arranged at equal intervals in the circumferential direction of the outside peripheral wall 112 so that the end part of the one outside introducing port 170 is overlapped on the other outside introducing port 170, a quantity of exhaust gas which enters the gas separating chamber 119 from the outside introducing ports 170 is sufficient and a response of a detection value of a sensing element 10 to the exhaust gas is not delayed. Further, since all the outside introducing ports 170 are formed at the positions nearer to the front end side than the positions where the inside introducing ports 125 of the inside protector 120 are formed in the axial direction O, water droplets which enter the gas separating chamber 119 from the outside introducing ports 170 can be prevented from entering a gas detecting chamber 129 from the inside introducing ports 125 of the inside protector 120. Further, since the outside introducing ports 170 are provided over an entire periphery of the outside peripheral wall 112 of the outside protector 110, a rotating angle for attachment of the gas sensor 1 to an exhaust gas passage is not limited.

In the above-described first to third exemplary embodiments, when a circular section formed by cutting the outside protector 110 by a plane which is perpendicular to the axial direction O and passes the outside introducing ports 170 is divided into a plurality of parts by a straight line passing through a center thereof, at least one outside introducing port 170 is present in each of the divided areas. For instance, in the first exemplary embodiment, when the outside peripheral wall 112 of the outside protector 110 is divided by two straight lines perpendicular to each other, at least one outside introducing port 170 is present in each of the divided areas.

Figure 8:
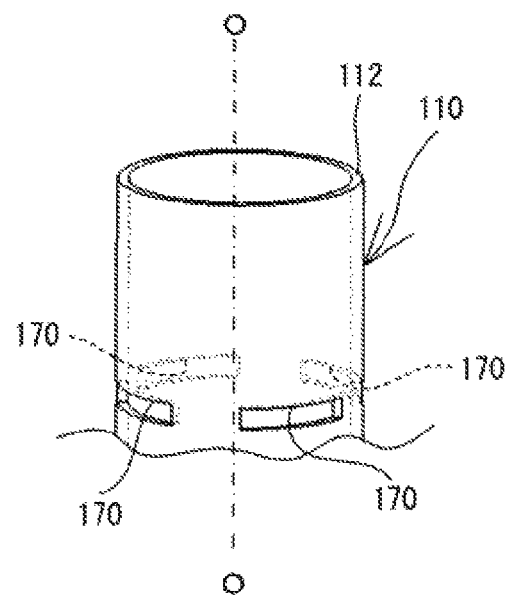
FIG. 8 is a perspective view of an outside protector 110.
Figure 9:
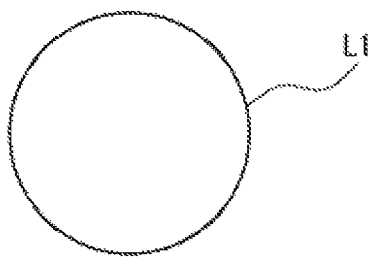
FIG. 9 is a plan view showing a circumference length L1 of an outside peripheral wall 112 of the outside protector 110.
Figure 10:
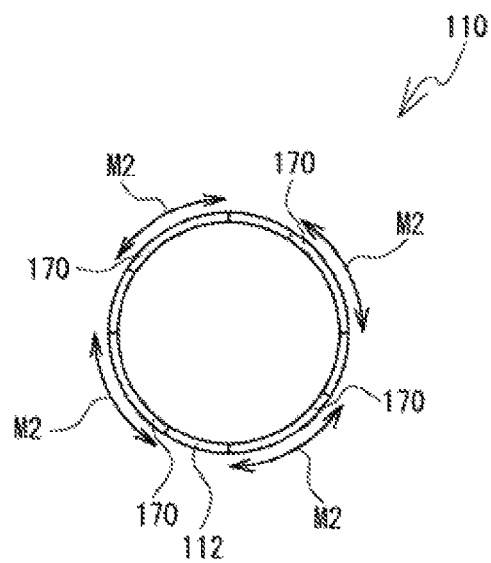
FIG. 10 is a plan view showing individual lengths M2 of outside introducing ports 170 in the circumferential direction of the outside peripheral wall 112 when the outside protector 110 is projected on a plane vertical to an axis O.

Now, with reference to FIG. 8 to FIG. 13, a definition of the lateral hole of the outside introducing port 170 will be described below. Initially, as shown in FIG. 8, an example will be described that four outside introducing ports 170 of rectangular lateral holes which are crosswise long in front view are formed in one row in the circumferential direction of the outside peripheral wall 112 of the outside protector 110. The outside introducing port 170 has a crosswise long rectangular form in front view. When the outside protector 110 is projected on a plane vertical to the axis O, the length of a circumference of the outside peripheral wall 112 of the outside protector 110 is supposed to be set to L1 (see FIG. 9). Further, as shown in FIG. 10, when the outside protector 110 is projected on the plane vertical to the axis O, assuming that an individual length of the outside introducing port 170 in the circumferential direction of the outside peripheral wall 112 is M2 and the total of the individual lengths of the four outside introducing ports 170 in the circumferential direction of the outside peripheral wall 112 is L2, L2 is expressed by L2=M2×4. Here, in the example shown in FIG. 8, L2/L1=0.58 is established.

Figure 11:
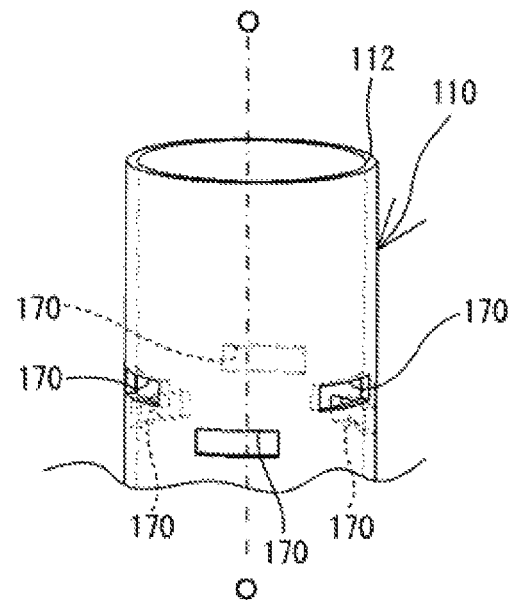
FIG. 11 is a perspective view of an outside protector 110.
Figure 12:
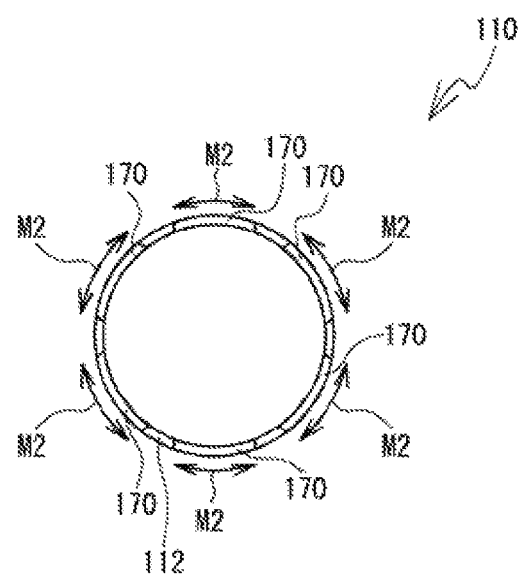
FIG. 12 is a plan view showing individual lengths M2 of outside introducing ports 170 in the circumferential direction of an outside peripheral wall 112 when the outside protector 110 is projected on a plane vertical to an axis O.

Then, as shown in FIG. 11, an example will be described that six outside introducing ports 170 of rectangular lateral holes which are crosswise long in front view are respectively formed in two upper and lower rows in the circumferential direction of the outside peripheral wall 112 of the outside protector 110. Also here, when the outside protector 110 is projected on a plane vertical to the axis O, the length of a circumference of the outside peripheral wall 112 of the outside protector 110 is supposed to be set to L1 (see FIG. 9). Further, as shown in FIG. 12, when the outside protector 110 is projected on the plane vertical to the axis 0, assuming that an individual length of the outside introducing port 170 in the circumferential direction of the outside peripheral wall 112 is set to M2 and the total of the lengths of the six outside introducing ports 170 in the circumferential direction of the outside peripheral wall 112 is set to L2, L2 is expressed by L2=M2×6. Here, in the example shown in FIG. 12, L2/L1=0.66 is established.

Figure 13:
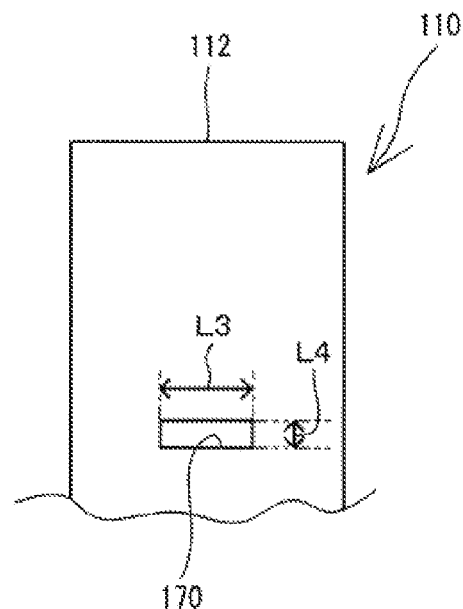
FIG. 13 is a front view of the outside introducing port 170.

Subsequently, as shown in FIG. 13, a length of one outside introducing port 170 in the circumferential direction of the outside protector 110 is set to L3, a length in the axial direction O is set to L4 and a ratio of a crosswise length to a longitudinal length (an aspect ratio) of the outside introducing port 170 is set to L3/L4. In the present invention, the lateral hole corresponds to either "L/L1≥0.52" or "L3/L4≥3". Accordingly, the outside introducing port 170 is formed on the outside peripheral wall 112 of the outside protector 110 so that the outside introducing port 170 corresponds to either "L2/L1≥0.52" or "L3/L4≥3".

Then, using the first exemplary embodiment to the third exemplary embodiment, a first comparative example (see FIG. 14 and FIG. 15), a second comparative example (see FIG. 16) and a third comparative example (FIG. 17), a result of a first analysis simulation of a responsiveness of the gas sensor 1 will be described with reference to a graph of FIG. 18.

Initially, an outside protector 110 of the first comparative example will be described with reference to FIG. 14 and FIG. 15. The outside protector 110 of the first comparative example is an outside protector of a conventional technique having outside introducing ports 170 of usual forms. Specifically, on an outside peripheral wall 112 of the outside protector 110, the eight outside introducing ports 170 are formed at prescribed intervals along a circumferential direction. The outside introducing ports 170 are formed at positions nearer to a front end side than positions where inside introducing ports 125 of an inside protector 120 are formed in an axial direction O. Further, the outside introducing ports 170 are formed in shapes of longitudinal holes in which opening lengths in the direction (the axial direction O) perpendicular to the circumferential direction are larger than opening lengths in the circumferential direction of the outside peripheral wall 112.

Figure 16:
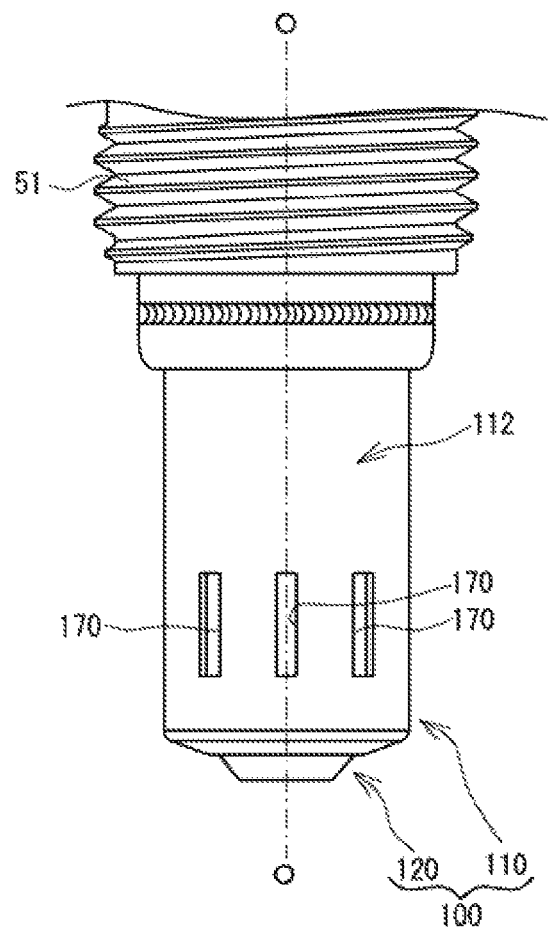
FIG. 16 is front view of a protector 100 according to a second comparative example.

Then, with reference to FIG. 16, forms of outside introducing ports 170 of an outside protector 110 of the second comparative example will be described below. In the outside protector 110 of the second comparative example, the outside introducing ports 170 have opening lengths in the circumferential direction of an outside peripheral wall 112 smaller than those of the first comparative example. Namely, the outside introducing ports 170 of the second comparative example are formed to be more elongated than those of the first comparative example.

Figure 17:
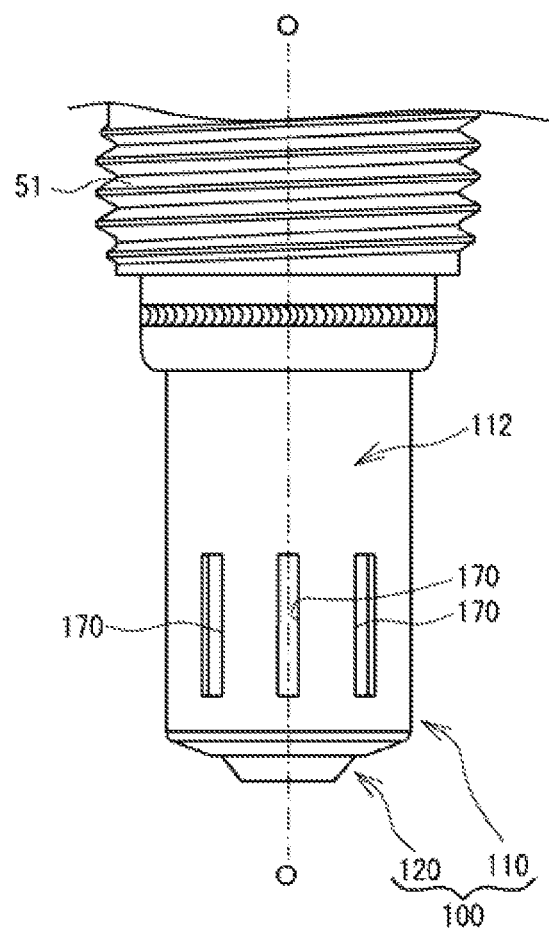
FIG. 17 is front view of a protector 100 according to a third comparative example.

Then, with reference to FIG. 17, forms of outside introducing ports 170 of an outside protector 110 of the third comparative example will be described below. In the outside protector 110 of the third comparative example, the outside introducing ports 170 have opening lengths in the circumferential direction of an outside peripheral wall 112 smaller than those of the first comparative example and lengths in an axial direction O larger than those of the first comparative example and the second comparative example. Namely, the outside introducing ports 170 of the third comparative example are formed to be more elongated than those of the first comparative example and the second comparative example.

In the first analysis simulation, a total opening area of all the outside introducing ports 170 of the outside protector 110 of the first comparative example is set to 1. A total opening area of all the outside introducing ports 170 of the outside protector 110 according to the first exemplary embodiment is set to "0.6". A total opening area of all the outside introducing ports 170 of the outside protector 110 according to the second exemplary embodiment is set to "0.5". In the outside protector 110 according to the third exemplary embodiment, a total opening area of all the outside introducing ports 170 is set to "0.8". Further, in the outside protector 110 of the second comparative example, a total opening area of all the outside introducing ports 170 is set to "0.5". In the outside protector 110 of the third comparative example, a total opening area of all the outside introducing ports 170 is set to "0.8". According to this condition, a responsiveness of the sensing element 10 (a relation between a rate of replacement of element gas and time (second)) is simulated by a computer. The result of the first analysis simulation is shown in the graph of FIG. 18.

Figure 18:
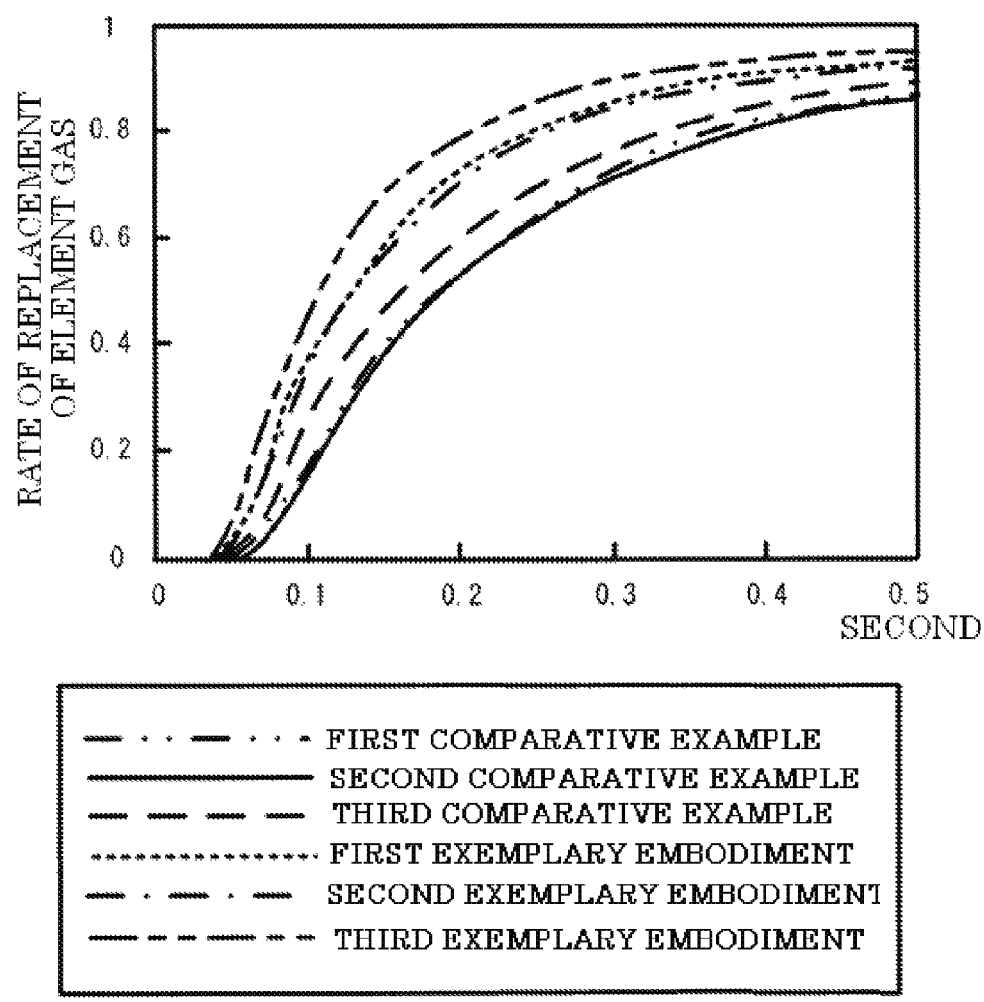
FIG. 18 is a graph of a result of a first analysis simulation.

As shown in the graph of FIG. 18, it is understood that the second comparative example has the worst responsiveness. Next, the first comparative example and the third comparative example are worse in their responsiveness. As compared therewith, it is understood that the third exemplary embodiment has the best responsiveness. Subsequently, it is understood that the first exemplary embodiment and the second exemplary embodiment are better in their responsiveness. Accordingly, it is recognized that by forming the outside introducing ports 170 with the shapes of the lateral holes, the opening areas may be more reduced to obtain a higher responsiveness than the outside introducing ports 170 formed in the shapes of the longitudinal holes as in the conventional technique.

Figure 19:
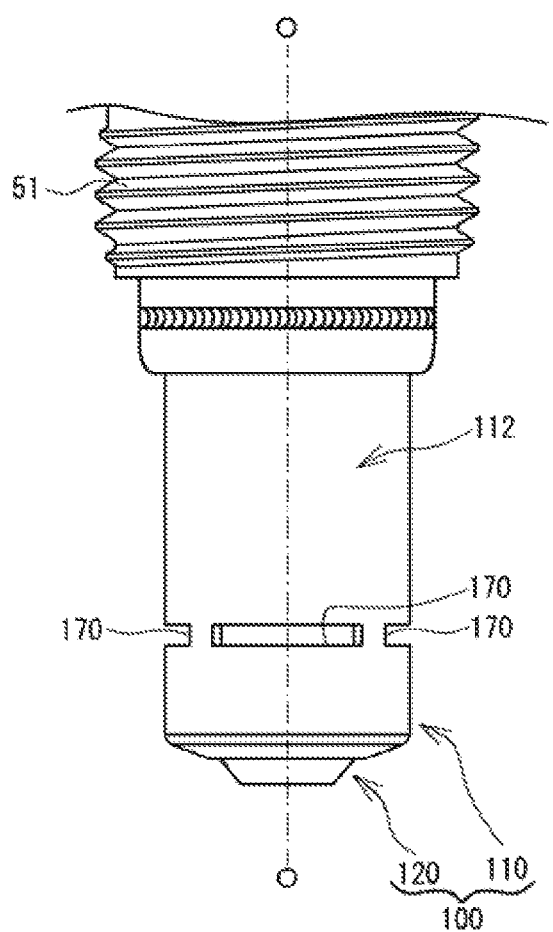
FIG. 19 is a front view of a protector 100 according to a fourth exemplary embodiment.
Figure 20:
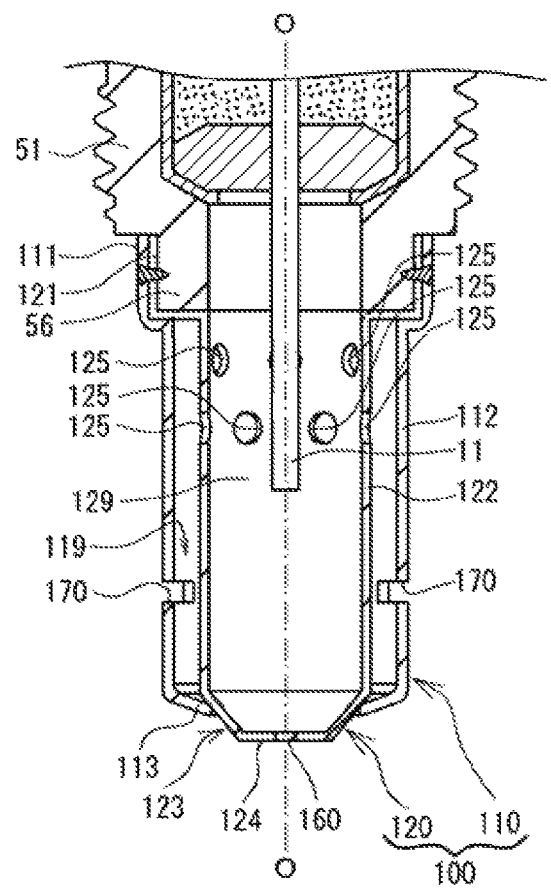
FIG. 20 is a longitudinally sectional view of the protector 100 according to the fourth exemplary embodiment in the same direction as that of the section shown in FIG. 1.
Figure 21:
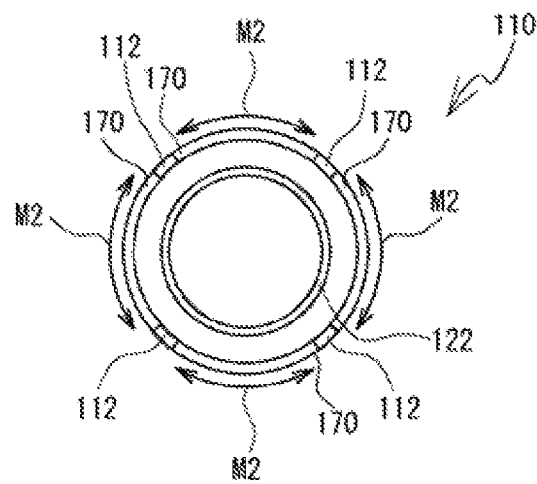
FIG. 21 is a cross-sectional view of the protector 100 according to the fourth exemplary embodiment.
Figure 22:
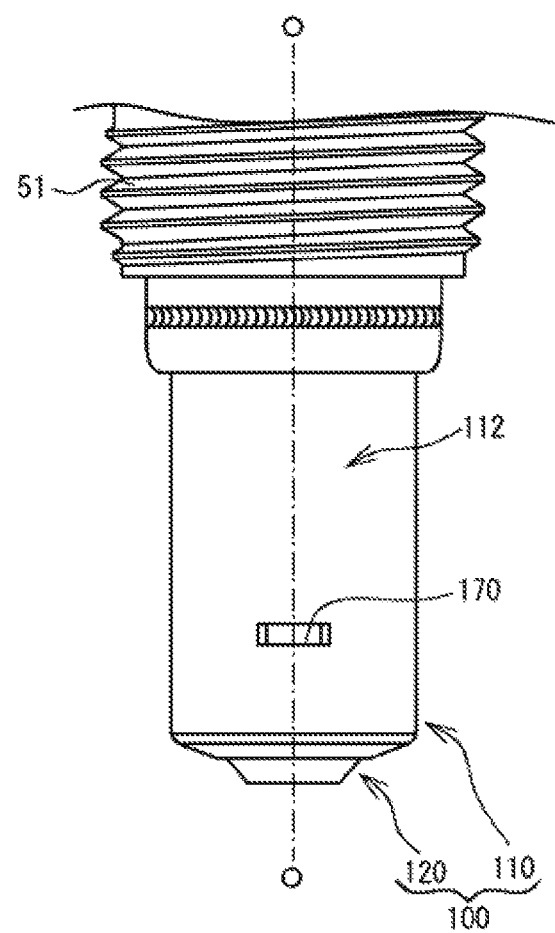
FIG. 22 is a front view of a protector 100 according to a fifth exemplary embodiment.
Figure 23:
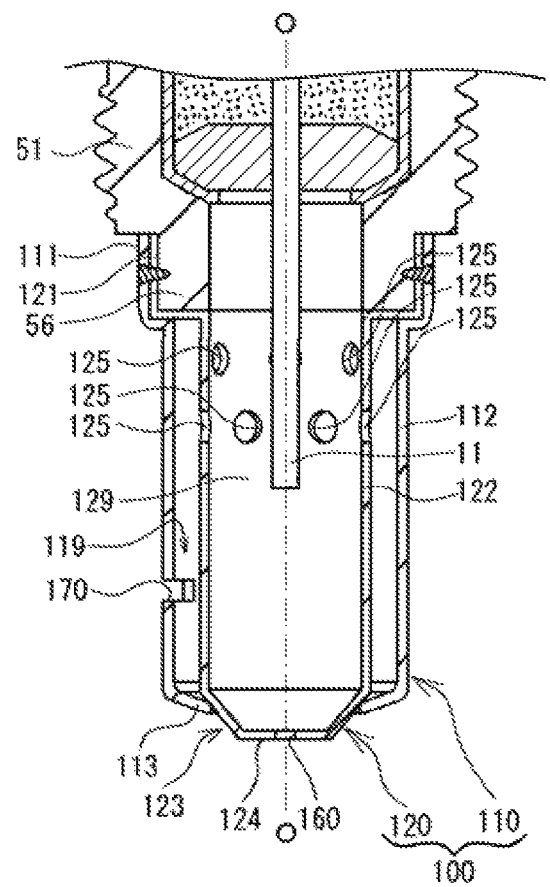
FIG. 23 is a longitudinally sectional view of the protector 100 according to the fifth exemplary embodiment in the same direction as that of the section shown in FIG. 1.
Figure 24:
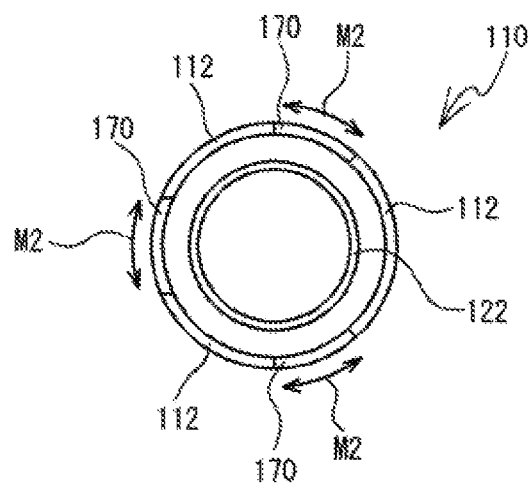
FIG. 24 is a cross-sectional view of the protector 100 according to the fifth exemplary embodiment.

Subsequently, as for a rate of the outside introducing ports 170 in the circumferential direction of the outside peripheral wall 112 of the outside protector 110, a result of a second analysis simulation of a responsiveness of a gas sensor 1 according to a fourth exemplary embodiment shown in FIG. 19 to FIG. 21 and a fifth exemplary embodiment shown in FIG. 22 to FIG. 24 will be described below with reference to a graph of FIG. 25.

Now, with reference to FIG. 19 to FIG. 21, a structure of an outside introducing port 170 of an outside protector 110 according to the fourth exemplary embodiment will be described below. A plurality of outside introducing ports 170 through which an external part of the outside protector 110 communicates with a gas separating chamber 119 are formed along a circumferential direction in an outside peripheral wall 112 of the outside protector 110 according to the fourth exemplary embodiment. The outside introducing ports 170 extend in the circumferential direction of the outside peripheral wall 112 and are formed in shapes of lateral holes in which opening lengths in the circumferential direction are larger than opening lengths in the direction perpendicular to the circumferential direction. Further, the four outside introducing ports 170 are formed in one row in the circumferential direction of the outside peripheral wall 112. As shown in FIG. 21, a length of each of the outside introducing ports 170 in the circumferential direction of the outside peripheral wall 112 is supposed to be set to M2 and a length of a circumference of the outside peripheral wall 112 is supposed to be set to L1. L2=M2×4 is supposed to be established. In the fourth exemplary embodiment, a rate of an opening in the circumferential direction of the outside peripheral wall 112 is supposed to be set to L2/L1=0.83.

Then, with reference to FIG. 22 to FIG. 24, a structure of an outside introducing port 170 of an outside protector 110 according to the fifth exemplary embodiment will be described below. In an outside peripheral wall 112 of the outside protector 110 according to the fifth exemplary embodiment, a plurality of outside introducing ports 170 through which an external part of the outside protector 110 communicates with a gas separating chamber 119 are formed along a circumferential direction. The outside introducing ports 170 extend in the circumferential direction of the outside peripheral wall 112 and formed in shapes of lateral holes in which opening lengths in the circumferential direction are larger than opening lengths in the direction perpendicular to the circumferential direction. Further, the three outside introducing ports 170 are formed in one row in the circumferential direction of the outside peripheral wall 112. However, the opening lengths in the circumferential direction are not so large. As shown in FIG. 24, a length of each of the outside introducing ports 170 in the circumferential direction of the outside peripheral wall 112 is supposed to be set to M2 and a length of a circumference of the outside peripheral wall 112 is supposed to be set to L1. L2=M2×3 is supposed to be established. In the fifth exemplary embodiment, a rate of an opening in the circumferential direction of the outside peripheral wall 112 is supposed to be set to L2/L1=0.30.

Figure 14:
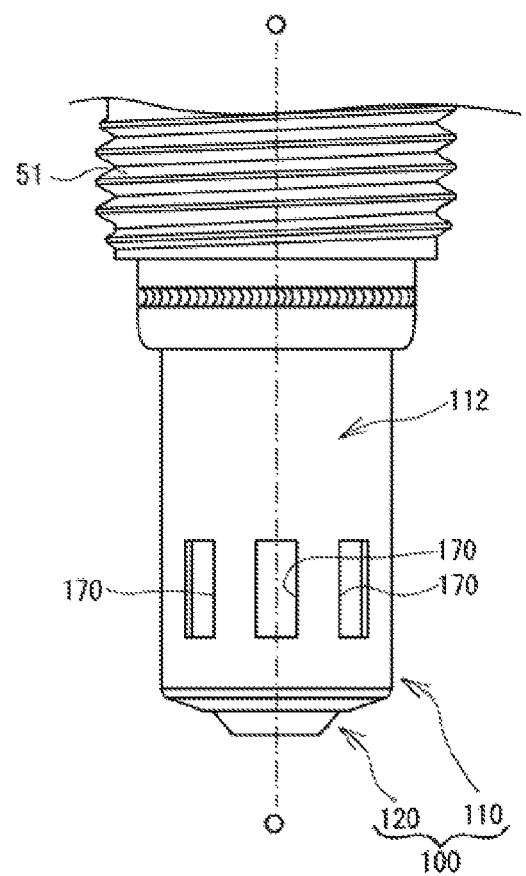
FIG. 14 is a front view of a protector 100 of a first comparative example (a conventional technique).
Figure 15:
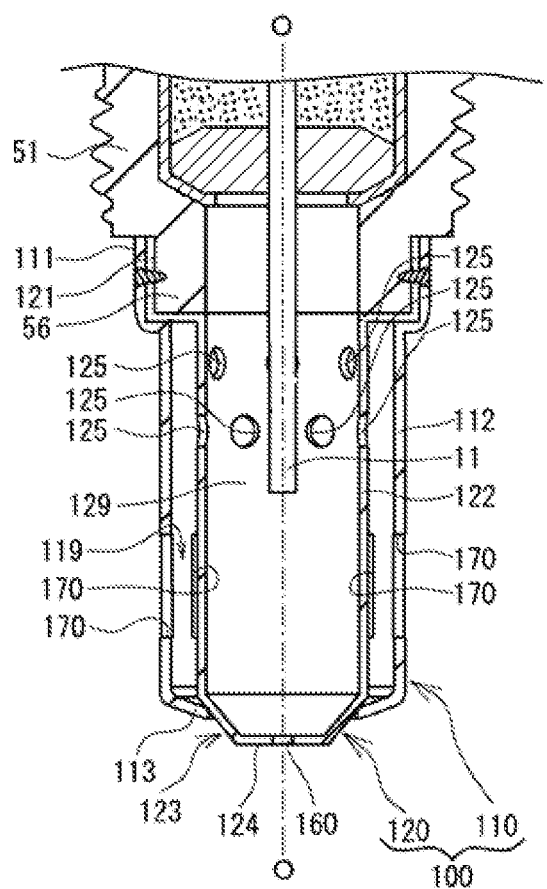
FIG. 15 is a longitudinally sectional view of the protector 100 of the first comparative example (the conventional technique) in the same direction as that of the section shown in FIG. 1.

In the second analysis simulation, by using the outside protector 110 of the first comparative example shown in FIG. 14 and FIG. 15, the outside protector 110 according to the above-described fourth exemplary embodiment and the outside protector 110 according to the fifth exemplary embodiment, a responsiveness of the sensing element 10 (a relation between a rate of replacement of element gas and time (second)) is simulated by a computer. The result of the second analysis simulation is shown in the graph of FIG. 25.

Figure 25:
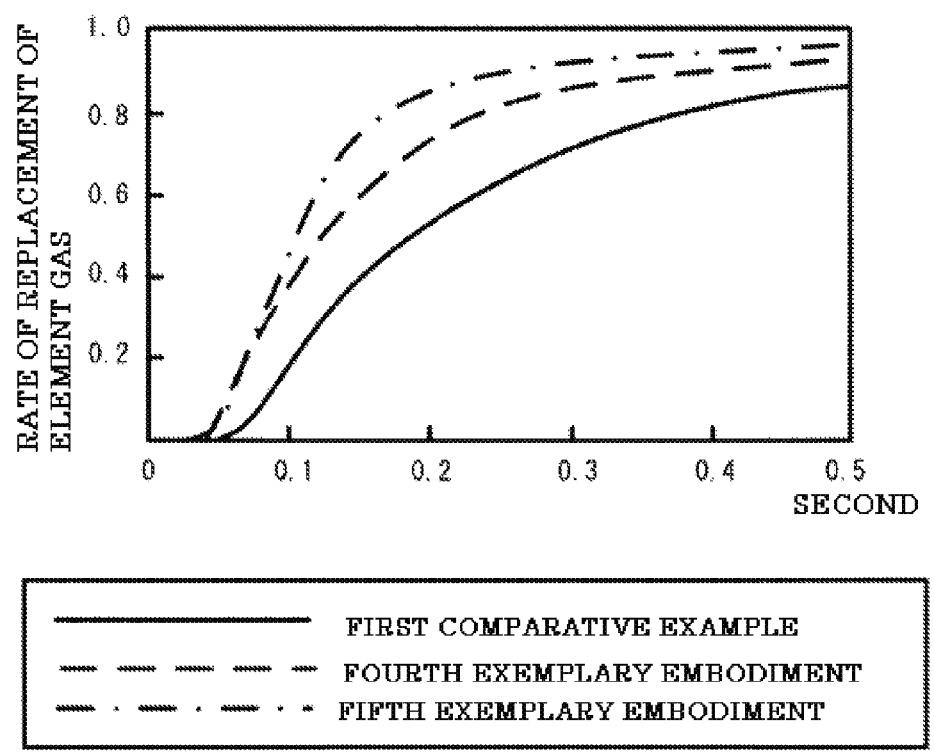
FIG. 25 is a graph of a result of a second analysis simulation.
Figure 26:
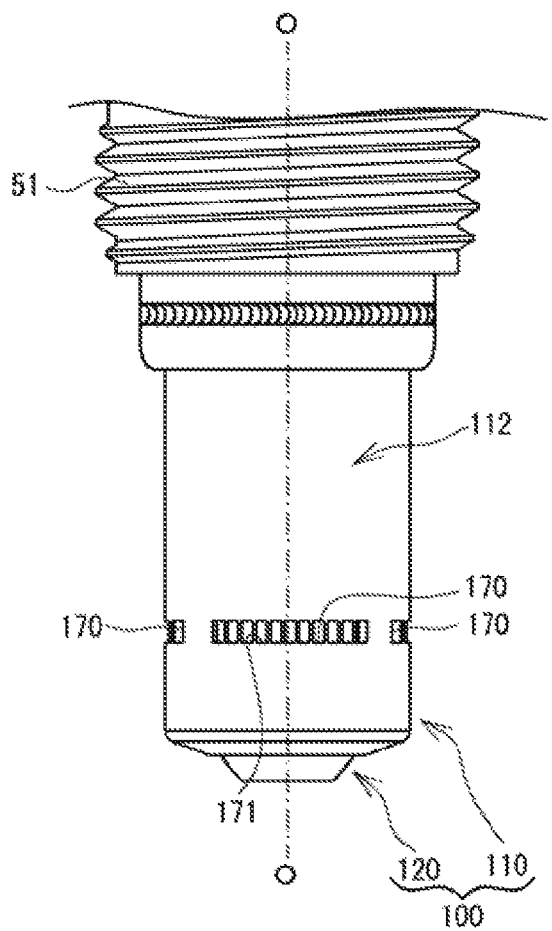
FIG. 26 is a front view of a modified example of an outside introducing port 170.

As shown in the graph of FIG. 25, it is understood that the first comparative example has the worst responsiveness. As compared therewith, it is understood that the fifth exemplary embodiment has the best responsiveness. Subsequently, it is understood that the fourth exemplary embodiment is better in its responsiveness. Accordingly, it can be decided that when the rate (L2/L1) of the opening in the circumferential direction of the outside peripheral wall 112 of the outside protector 110 is 0.30 (30%) or higher, the responsiveness of the sensing element 10 is not deteriorated.

Figure 27:
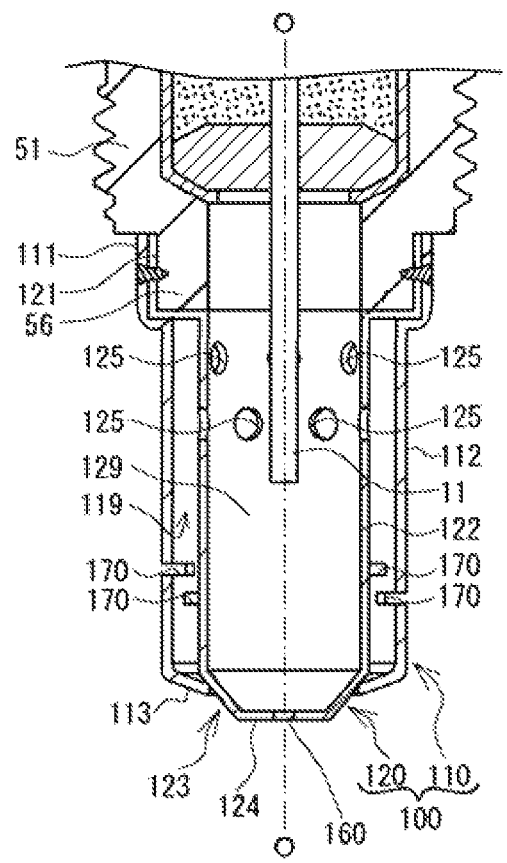
FIG. 27 is a longitudinally sectional view of a protector 100 of a fourth comparative example in the same direction as that of the section shown in FIG. 1.
Figure 28:
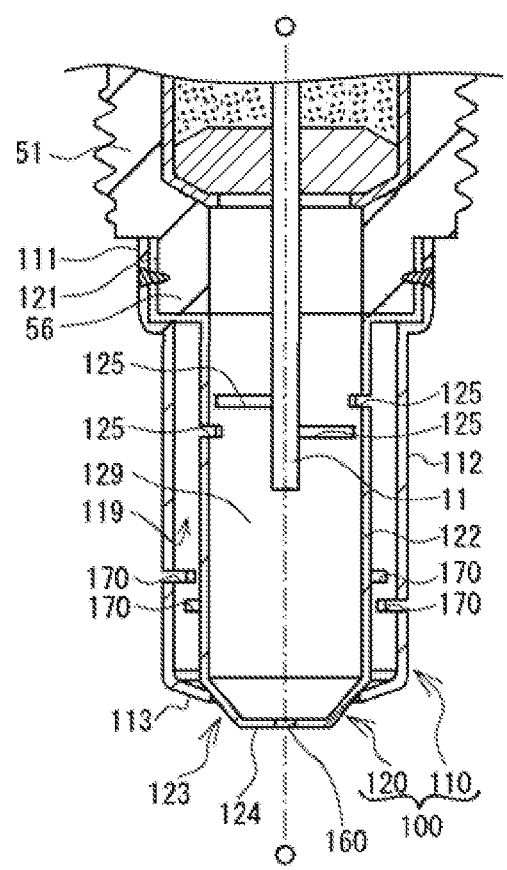
FIG. 28 is a longitudinally sectional view of a protector 100 according to a sixth exemplary embodiment in the same direction as that of the section shown in FIG. 1.
Figure 29:
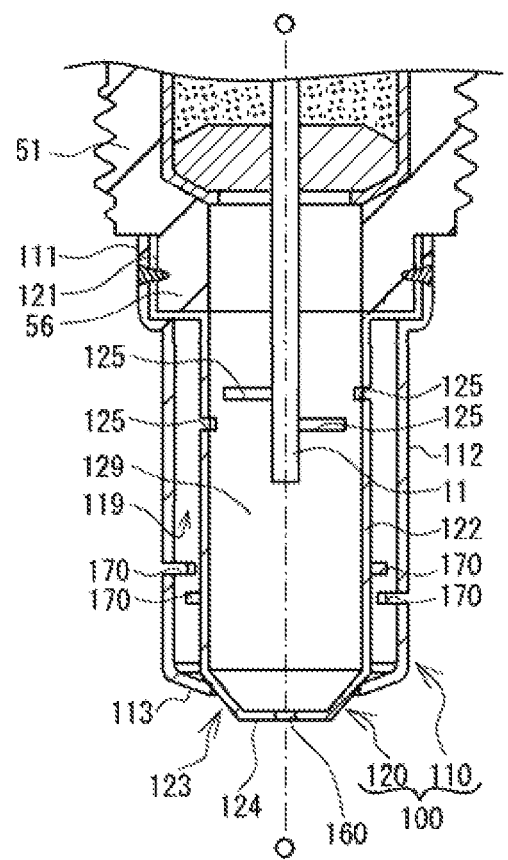
FIG. 29 is a longitudinally sectional view of a protector 100 according to a seventh exemplary embodiment in the same direction as that of the section shown in FIG. 1.
Figure 30:
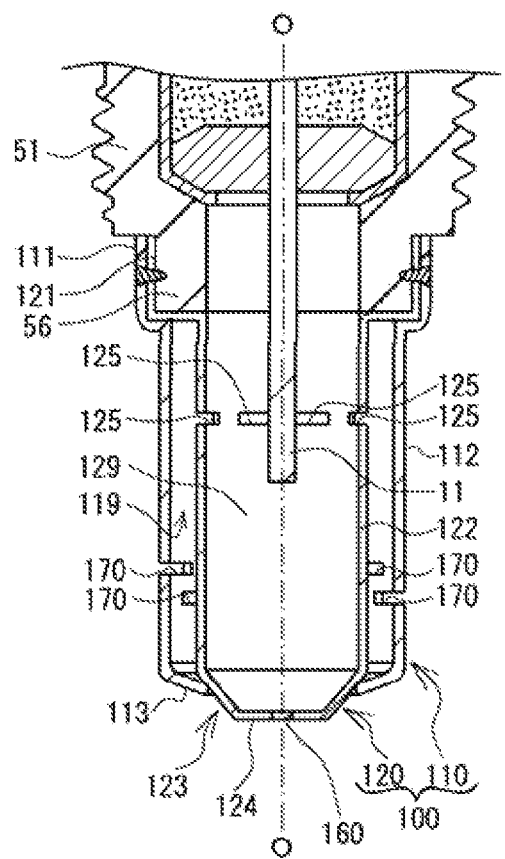
FIG. 30 is a longitudinally sectional view of a protector 100 according to an eighth exemplary embodiment in the same direction as that of the section shown in FIG. 1.

Now, as for a case that areas of opening parts of the inside introducing ports 125 in the circumferential direction of the inside peripheral wall 122 of the inside protector 120 are changed, a structure of the gas sensor 1 will be described below by using a fourth comparative example shown in FIG. 27, a sixth exemplary embodiment shown in FIG. 28, a seventh exemplary embodiment shown in FIG. 29 and an eighth exemplary embodiment shown in FIG. 30.

Initially, with reference to FIG. 27, an outside protector 110 and an inside protector 120 of the fourth comparative example will be described below, a plurality of outside introducing ports 170 through which an external part of the outside protector 110 communicates with a gas separating chamber 119 are formed along a circumferential direction in an outside peripheral wall 112 of the outside protector 110 of the fourth comparative example. The outside introducing ports 170 extend in the circumferential direction of the outside peripheral wall 112 and are formed in shapes of lateral holes in which opening lengths in the circumferential direction are larger than opening lengths in the direction perpendicular to the circumferential direction. The outside introducing ports 170 are formed in two rows in an axial direction O on the outside peripheral wall 112. The outside introducing ports 170 are arranged at equal intervals in the circumferential direction of the outside peripheral wall 112 so that an end part of the one outside introducing port 170 is overlapped on the other outside introducing port 170 in the axial direction O. All the outside introducing ports 170 are formed at positions nearer to a front end side than positions where inside introducing ports 125 of the inside protector 120 are formed in the axial direction O. Namely, the positions of rear ends of the outside introducing ports 170 are arranged nearer to the front end side than the positions of front ends of the inside introducing ports 125.

In an inside peripheral wall 122 of the inside protector 120, twelve pieces of inside introducing ports 125 as circular holes are opened along the circumferential direction at positions near to a base end part 121 in the axial direction O. The inside introducing ports 125 are holes which mainly introduce a gas component of exhaust gas introduced to the gas separating chamber 119 through the outside introducing ports 170 of the outside protector 110 to an inner part of the inside protector 120, namely, a gas detecting chamber 129 to which a detecting part 11 of a sensing element 10 is exposed. In the fourth comparative example, the six inside introducing ports 125 are formed in the circumferential direction and in two rows on the outside peripheral wall 112 in the axial direction O. As one example, a diameter of one inside introducing port 125 is set to 1.5 mm. A total of areas of the opening parts of the twelve inside introducing ports 125 are 21.2 mm$^2$.

Now, with reference to FIG. 28, an inside protector 120 according to the sixth exemplary embodiment will be described below. Since an outside protector 110 according to the sixth exemplary embodiment has the same structure as that of the fourth comparative example, an explanation will be omitted. In an inside peripheral wall 122 of the inside protector 120 according to the sixth exemplary embodiment, a plurality of inside introducing ports 125 are opened along a circumferential direction at positions near to a base end part 121 in an axial direction O. The inside introducing ports 125 extend in the circumferential direction of the inside peripheral wall 122 and are formed in shapes of lateral holes in which opening lengths in the circumferential direction are larger than opening lengths in the direction perpendicular to the circumferential direction. Further, the inside introducing ports 125 are formed in two rows on the inside peripheral wall 122 in the axial direction O. Further, the inside introducing ports 125 are arranged at equal intervals in the circumferential direction of the inside peripheral wall 122 so that an end part of the one inside introducing port 125 is overlapped on the other inside introducing port 125 in the axial direction O. As one example, the one inside introducing port 125 has a width of 0.6 mm in the axial direction O. The inside introducing ports 125 are opened at 70° with respect to the axis O as a center in a plane perpendicular to the axis O. Three openings are formed in two rows. Accordingly, a total of areas of the opening parts of the inside introducing ports 125 according to the sixth exemplary embodiment is 16.7 mm$^2$. Accordingly, the ratio of the areas (21.2 mm$^2$) of the opening parts of the inside introducing ports 125 according to the sixth exemplary embodiment to the total is 0.79.

Further, though not shown in the drawing, when the inside protector 120 is projected on a plane vertical to the axis O, a length of a circumference of the inside peripheral wall 122 of the inside protector 120 is supposed to be set to L5. When the inside protector 120 is projected on a plane vertical to the axis O, an individual length of the inside introducing port 125 in the circumferential direction of the inside peripheral wall 122 is supposed to be set to M3 and a total of the lengths of the three inside introducing ports 125 in the circumferential direction of the inside peripheral wall 122 is supposed to be set to L6. Thus, L6=M3×3 is established. Further, when a length of the one inside introducing port 125 of the inside protector 120 in the circumferential direction is set to L7 and a length in the axial direction O is set to L8, a ratio of a crosswise length to a longitudinal length (an aspect ratio) of the inside introducing port 125 is set to L7/L8. Here, the inside introducing ports 125 are formed so as to establish L6/L5≥0.52" and "L7/L8≥3".

Then, with reference to FIG. 29, an inside protector 120 according to the seventh exemplary embodiment will be described below. Since an outside protector 110 according to the seventh exemplary embodiment has the same structure as that of the fourth comparative example, an explanation will be omitted. In an inside peripheral wall 122 of the inside protector 120 according to the seventh exemplary embodiment, a plurality of inside introducing ports 125 are opened along a circumferential direction at positions near to a base end part 121 in an axial direction O. The inside introducing ports 125 extend in the circumferential direction of the inside peripheral wall 122 and are formed in shapes of lateral holes in which opening lengths in the circumferential direction are larger than opening lengths in the direction perpendicular to the circumferential direction. Further, the inside introducing ports 125 are formed in two rows on the inside peripheral wall 122 in the axial direction O. The inside introducing ports 125 are arranged at equal intervals in the circumferential direction of the inside peripheral wall 122 so that positions where the inside introducing ports 125 are formed are shifted in the upper and lower sides. As one example, the one inside introducing port 125 has a width of 0.6 mm in the axial direction O. The inside introducing ports 125 are opened at 45° with respect to the axis O as a center in a plane perpendicular to the axis O. Three openings are formed in the two rows. Thus, a total of areas of the opening parts of the inside introducing ports 125 according to the seventh exemplary embodiment is 10.7 mm². Accordingly, the ratio of the areas (21.2 mm²) of the opening parts of the inside introducing ports 125 according to the seventh exemplary embodiment to the total is 0.51.

Then, with reference to FIG. 30, an inside protector 120 according to the eighth exemplary embodiment will be described below. Since an outside protector 110 according to the eighth exemplary embodiment has the same structure as that of the fourth comparative example, an explanation will be omitted. In an inside peripheral wall 122 of the inside protector 120 according to the eighth exemplary embodiment, a plurality of inside introducing ports 125 are opened along a circumferential direction at positions near to a base end part 121 in an axial direction O. The inside introducing ports 125 extend in the circumferential direction of the inside peripheral wall 122 and are formed in shapes of lateral holes in which opening lengths in the circumferential direction are larger than opening lengths in the direction perpendicular to the circumferential direction. Further, the inside introducing ports 125 are formed in one row at equal intervals in the circumferential direction of the inside peripheral wall 122. As one example, the one inside introducing port 125 has a width of 0.6 mm in the axial direction O. The inside introducing ports 125 are opened at 70° with respect to the axis O as a center in a plane perpendicular to the axis O. Four openings are formed in the one row. Thus, a total of areas of the opening parts of the inside introducing ports 125 according to the eighth exemplary embodiment is 11.1 mm². Accordingly, the ratio of the areas (21.2 mm²) of the opening parts of the inside introducing ports 125 according to the eighth exemplary embodiment to the total is 0.53.

Subsequently, with reference to FIG. 31, a result of a third analysis simulation of a responsiveness of the gas sensor 1 will be described below. In the third analysis simulation, the responsiveness of the sensing element 10 (a relation between a rate of replacement of element gas and time (second)) is simulated by a computer by using the fourth comparative example and the sixth exemplary embodiment to the eighth exemplary embodiment.

Figure 31:
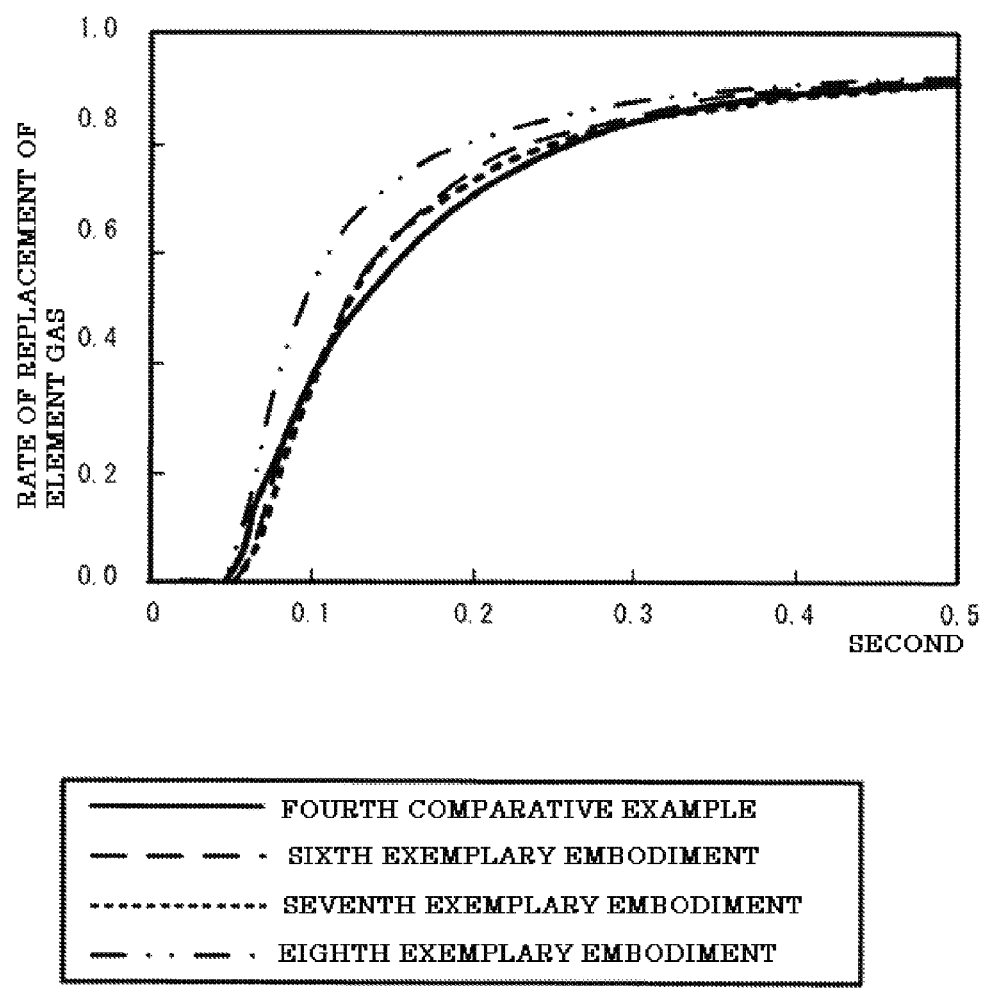
FIG. 31 is a graph of a result of a third analysis simulation.

As shown in the graph of FIG. 31, it is understood that the responsiveness of any of the sixth exemplary embodiment, the seventh exemplary embodiment and the eighth exemplary embodiment is not deteriorated relative to the responsiveness of the fourth comparative example. It is especially recognized that the eighth exemplary embodiment has the best responsiveness. Accordingly, it is recognized that even when the total of the areas of the opening parts of the inside introducing ports 125 of the inside protector 120 is reduced to about 50% as small as the total of the areas of the opening parts of the fourth comparative example, the responsiveness of the sensing element 10 is not deteriorated.

Figure 32:
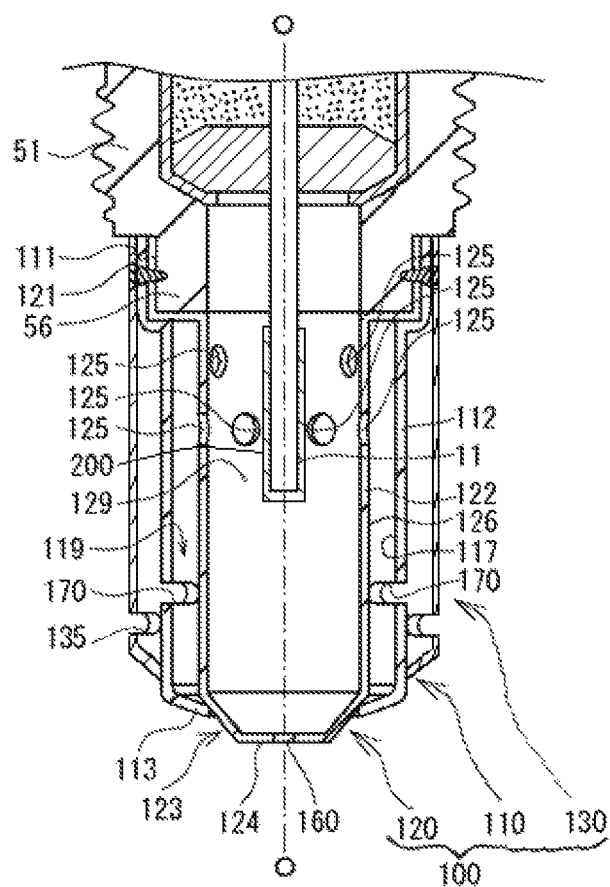
FIG. 32 is a longitudinally sectional view of a protector 100 according to a ninth exemplary embodiment in the same direction as that of the section shown in FIG. 1.

Now, referring to FIG. 32, a protector 100 according to a ninth exemplary embodiment will be described below. The protector 100 according to the ninth exemplary embodiment is formed by a triple protector including an outside protector 110, an inside protector 120 and a second outside protector 130. Also in the second outside protector 130, second outside introducing ports 135 are formed which have the same configurations as those of outside introducing ports 170. In this case, a sensing element 10 can be more assuredly prevented from being covered with water by the second protector 130. Further, as shown in FIG. 32, a front end side of a detecting part 11 opposed to inside introducing ports 125 may be covered with a porous protective coat 200. In this case, the sensing element 10 can be more assuredly prevented from being covered with water by the porous protective coat 200.

The protector 100 shows one example of the "protector" of the present invention. The outside protector 110 and the second outside protector 130 show one examples of the "outside protector" of the present invention. The inside protector 120 indicates one example of the "inside protector" of the present invention. The outside introducing port 170 and the second outside introducing port 135 indicate one examples of the "introducing port formed in the outside protector" of the present invention. The gas separating chamber 119 shows one example of the "cavity" and a "gas passage" of the present invention.

The present invention is not limited to the above-described exemplary embodiments and various kinds of modifications may be made. For instance, the outside introducing port 170 is not limited to a simple lateral hole as shown in FIG. 2. The outside introducing port may be a hole part 170 corresponding to a lateral hole which is formed in such a way that a plurality of small rectangular holes 171 are closely and continuously formed in a circumferential direction of an outside peripheral wall 112 of an outside protector 110. In this case, strength of a part of the outside introducing port 170 is not deteriorated and an introducing efficiency of exhaust gas to the outside protector 110 is not deteriorated. Further, the sensing element 10 can be assuredly prevented form being covered with water. Accordingly, water droplets can be prevented from adhering to the sensing element 10 to break the sensing element. The number of the outside introducing ports 170 is not limited to the numbers of the above-described exemplary embodiments and may be set to a suitable number. Further, the above-described modifications are not limited to the outside introducing port 170 and may be applied to the second outside introducing port 135 or the inside introducing port 125.

INDUSTRIAL APPLICABILITY

The present invention may be similarly applied to a protector used in an oxygen sensor, an NOx sensor, an HC sensor, a temperature sensor or the like.

[Description of Reference Numerals and Signs]

1 gas sensor
10 sensing element
11 detecting part
50 metal shell
56 front end engaging part
100 protector
110 outside protector
112 outside peripheral wall
119 gas separating chamber
120 inside protector
122 inside peripheral wall
125 inside introducing port
129 gas detecting chamber
130 second outside protector
135 second outside introducing port
170 outside introducing port
171 hole
200 porous protective coat

What is claimed is:

1. A gas sensor including:
a sensing element which extends in an axial direction and has in a front end side a detecting part configured to detect a specific gas component in gas to be detected;
a metal shell which surrounds and holds a periphery of the sensing element in a radial direction under a state that the detecting part is allowed to protrude from a front end part of the metal shell;
an inside protector which includes an inside peripheral wall, a front end wall provided at a front end side of the inside protector, inside introducing ports formed at positions opposed to the sensing element on the inside peripheral wall to introduce the gas to an inner part of the inside protector and an opening end part provided at a base end side of the inside protector, the opening end part being fixed to the front end part of the metal shell under a state that the detecting part is accommodated so as to directly face the inner part of the inside protector; and
an outside protector which includes an outside peripheral wall that surrounds the inside peripheral wall with a cavity provided between the inside peripheral wall and the outside peripheral wall and includes outside introducing ports formed on the outside peripheral wall to introduce the gas into the cavity,
wherein either the plurality of inside introducing ports or the plurality of outside introducing ports are provided in a circumferential direction of at least one of the inside peripheral wall and the outside peripheral wall and are formed in shapes of lateral holes in which opening lengths in the circumferential direction are larger than opening lengths in the direction perpendicular to the circumferential direction,
wherein the plurality of outside introducing ports are formed in plural rows in the axial direction, and
wherein all of the plurality of outside introducing ports are arranged nearer to the front end side than positions of front ends of the inside introducing ports.

2. The gas sensor according to claim 1, wherein when L1 represents a length of an outer periphery of the outside peripheral wall, and L2 represents a total of lengths of the outside introducing ports in the circumferential direction when the outside peripheral wall is projected on a plane vertical to the axial direction, L2/L1 is 0.3 or more.

3. The gas sensor according to claim 1, wherein when L5 represents a length of an outer periphery of the inside peripheral wall, and L6 represents a total of lengths of the inside introducing ports in the circumferential direction when the inside peripheral wall is projected on a plane vertical to the axial direction, L6/L5 is 0.3 or more.

4. The gas sensor according to claim 2, wherein L2/L1 or L6/L5 is 0.52 or more.

5. The gas sensor according to claim 1, wherein when L3 represents a length of the outside introducing port in the circumferential direction of the outside peripheral wall and L4 represents a length of the outside introducing port in the direction perpendicular to L3, L3/L4 is 3 or more.

6. The gas sensor according to claim 1, wherein when L7 represents a length of the inside introducing port in the circumferential direction of the inside peripheral wall of the inside protector and L8 represents a length of the inside introducing port in the direction perpendicular to L7, L7/L8 is 3 or more.

7. The gas sensor according to claim 1, wherein when a circular section of the outside protector at a plane which is perpendicular to the axial direction and passes the outside introducing ports is divided into a plurality of parts by a straight line passing through a center of the circular section, at least one outside introducing port is present in each of the divided areas.

8. The gas sensor according to claim 1, wherein when a circular section of the inside protector at a plane which is perpendicular to the axial direction and passes the inside introducing ports is divided into a plurality of parts by a straight line passing through a center of the circular section, at least one inside introducing port is present in each of the divided areas.

9. The gas sensor according to claim 1, wherein the outside introducing port is formed by at least one of hole parts in the shapes of the lateral holes and the hole parts corresponding to the lateral holes.

10. The gas sensor according to claim 1, wherein the inside introducing port is formed by at least one of hole parts in the shapes of the lateral holes and the hole parts corresponding to the lateral holes.

11. The gas sensor according to claim 1, wherein the outside introducing ports are provided at other positions than positions opposed the inside introducing ports on the outside peripheral wall.

12. The gas sensor according to claim 1, wherein the outside introducing ports are provided nearer to the front end side in the axial direction on the outside peripheral wall than the inside introducing ports located nearest to the base end side.

13. The gas sensor according to claim 1, wherein the plurality of outside introducing ports are provided in the axial direction in the outside peripheral wall.

14. The gas sensor according to claim 1, wherein the plurality of inside introducing ports are provided in the axial direction in the inside peripheral wall.

15. The gas sensor according to claim 1, wherein the sensing element has a protective coat at least in positions opposed to the inside introducing ports.

* * * * *